United States Patent
Torrens Madrazo et al.

(10) Patent No.: US 6,309,873 B1
(45) Date of Patent: Oct. 30, 2001

(54) STREPTOKINASE MUTANTS

(75) Inventors: Isis del Carmen Torrens Madrazo; Jose de la Fuente Garcia; Ariana Garcia Ojalvo; Alina Seralena Menendez; Elder Pupo Escalona; Julio Raul Fernandez Masso; Martha de Jesus Gonzalez Griego, all of Habana (CU)

(73) Assignee: Centro de Ingenieria Genetica y Biotechnologia, C. Habana (CU)

( * ) Notice: Subject to any disclaimer, the term of this patent is extended or adjusted under 35 U.S.C. 154(b) by 0 days.

(21) Appl. No.: 09/374,038

(22) Filed: Aug. 13, 1999

(Under 37 CFR 1.47)

(30) Foreign Application Priority Data

Aug. 14, 1998  (CU) ..................................... 119/98

(51) Int. Cl.[7] .............. C12N 1/20; C12N 9/70; C12N 15/00; C12P 21/06
(52) U.S. Cl. .................... 435/216; 435/69.1; 435/320.1; 435/252.33; 424/192.1
(58) Field of Search ..................... 424/192.1; 435/69.1, 435/216, 466, 252.33, 320.1; 536/232

(56) References Cited

FOREIGN PATENT DOCUMENTS

489210 B1 * 11/1995 (EP) .

* cited by examiner

Primary Examiner—Rebecca E. Prouty
Assistant Examiner—Manjunath N. Rao
(74) Attorney, Agent, or Firm—Hoffmann & Baron, LLP

(57) ABSTRACT

The present invention is related to the field of biotechnology and genetic engineering techniques, particularly to a method for obtaining mutants obtain from streptokinase, to the molecules obtained from this method, as well as the expression vectors and microorganisms for recombinant obtaining. The object of the present invention is to achieve streptokinase mutants from modifications of skc-2 gene coding for streptokinase SKC-2 (Heberkinase®), such that the obtained mutants conserve their capacity for plasminogen activator complex formation having reduced antigenicity, that could constitute preferred alternatives to native streptokinase for thrombolytic therapy. The molecules obtained from present invention can be used in the treatment of disorders as myocardial infarct, pulmonary thromboembolism, surgical complications and other cases of thrombosis.

52 Claims, 14 Drawing Sheets

FIG. 1

Figure 2:
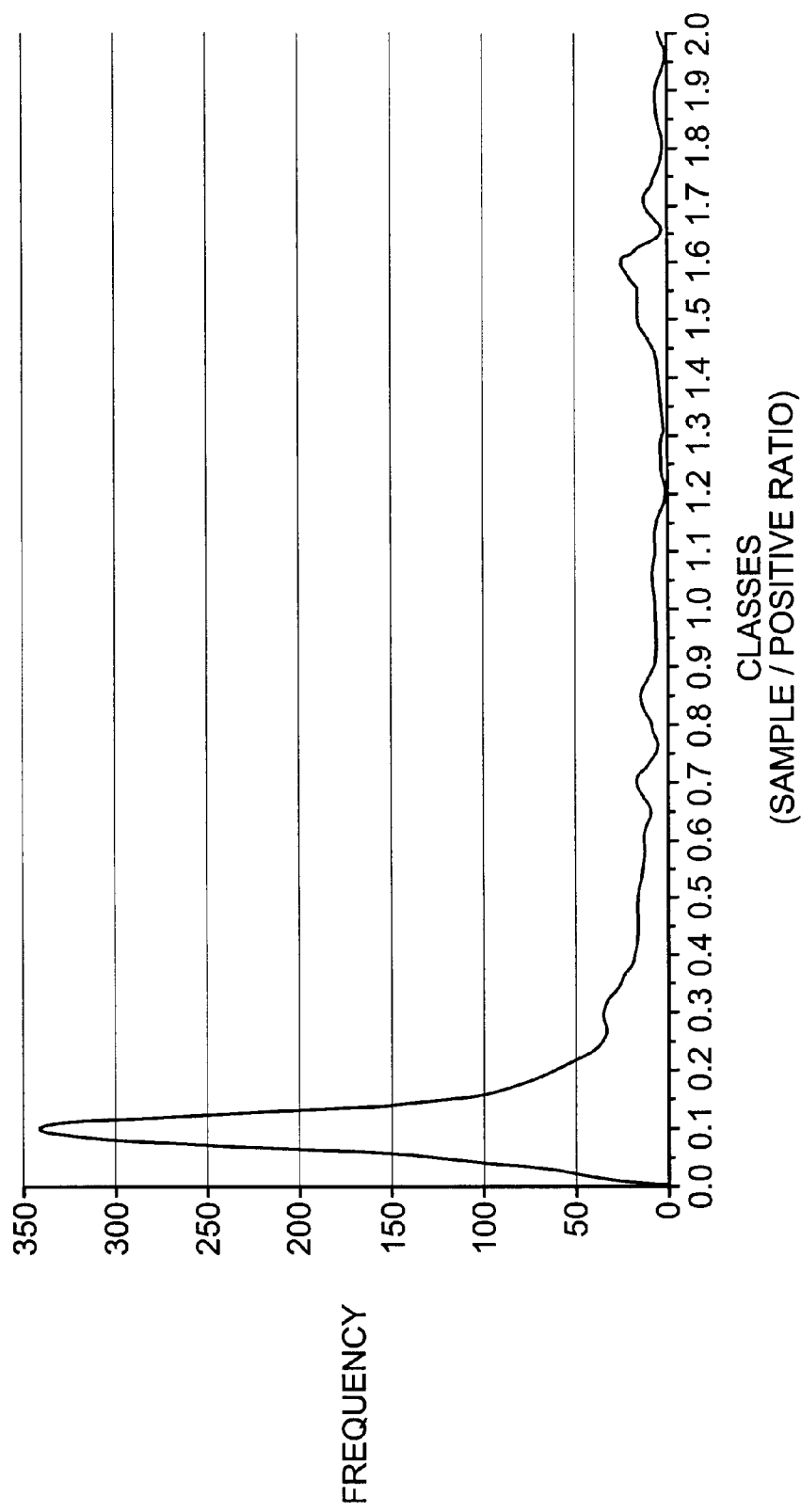

| SPOT | SKC-2 PEPTIDE | PEPTIDE SEQUENCE | PATIENT | | | | | | | | | | $N_1$ |
| | | | 5 | 6 | 7 | 12 | 14 | 17 | 28 | 32 | 42 | 46 | |
|---|---|---|---|---|---|---|---|---|---|---|---|---|---|
| 1 | 1-20 | IAGPEWLLDRPSVNNSQLVV | ▨ | ▨ | | ▨ | ▨ | ▨ | ▨ | | | | 6 |
| 2 | 10-29 | RPSVNNSQLVVSVAGTVEGT | | | | | | | | | | | |
| 3 | 20-39 | VSVAGTVEGTNQDISLKFFE | | | | | | | | | | | |
| 4 | 30-49 | NQDISLKFFEIDLTSRPAHG | | | | | | | | | | | |
| 5 | 40-59 | IDLTSRPAHGGKTEQGLSPK | | | | | | | | | | | |
| 6 | 50-69 | GKTEQGLSPKSKPFATDSGA | | | | | | | ▨ | ▨ | ▨ | | 3 |
| 7 | 60-79 | SKPFATDSGAMPHKLEKADL | | | | | | | ▨ | ▨ | ▨ | | 3 |
| 8 | 70-89 | MPHKLEKADLLKAIQEQLIA | | | | | | | | ▨ | | | 1 |
| 9 | 80-99 | LKAIQEQLIANVHSNDDYFE | | | | | | | | | | | |
| 10 | 90-109 | NVHSNDDYFEVIDFASDATI | | | | | | | | | | | |
| 11 | 100-119 | VIDFASDATITDRNGKVYFA | | | | | | | | | | | |
| 12 | 110-129 | TDRNGKVYFADKDGSVTLPT | | | | | | | | | | | |
| 13 | 120-139 | DKDGSVTLPTQPVQEFLLSG | | | | | | | | | | | |
| 14 | 130-149 | QPVQEFLLSGHVRVRPYKEK | ▨ | ▨ | ▨ | ▨ | ▨ | ▨ | ▨ | | ▨ | ▨ | 8 |
| 15 | 140-159 | HVRVRPYKEKPIQNQAKSVD | | | | | ▨ | | | | | | 1 |
| 16 | 150-169 | PIQNQAKSVDVEYTVQFTPL | | | | | | | | | | | |
| 17 | 160-179 | VEYTVQFTPLNPDDDFRPGL | | | | | | | | | | | |
| 18 | 170-189 | NPDDDFRPGLKDTKLLKTLA | ▨ | | ▨ | ▨ | ▨ | | | ▨ | | ▨ | 7 |
| 19 | 180-199 | KDTKLLKTLAIGDTITSQEL | | | | | | | | | | | |
| 20 | 190-209 | IGDTITSQELLAQAQSILNK | | | | | | | | | | | |
| 21 | 200-219 | LAQAQSILNKTHQGYTIYER | | | | | | | | | | | |
| 22 | 210-229 | THPGYTIYERDSSIVTHDND | | | | | | | | | | | |
| 23 | 220-239 | DSSIVTHDNDIFRTILPMDQ | | | | | | | | | | | |
| 24 | 230-249 | IFRTILPMDQEFTYHVKNRE | | | | | ▨ | | | | | | 1 |
| 25 | 240-259 | EFTYHVKNREQATEINKKSG | | | | | | ▨ | | | | | 1 |
| 26 | 250-269 | QATEINKKSGLNEEINNTDL | | | | | | | | | | ▨ | 1 |
| 27 | 260-279 | LNEEINNTDLISEKYYVLKK | ▨ | ▨ | ▨ | | | | | | | | 3 |
| 28 | 270-289 | ISEKYYVLKKGEKPYDPFDR | ▨ | ▨ | ▨ | | | | | | | | 3 |
| 29 | 280-299 | GEKPYDPFDRSHLKLFTIKY | ▨ | ▨ | ▨ | | | | | | | | 3 |
| 30 | 290-309 | SHLKLFTIKYVDVNTNELLK | | | | | ▨ | | | | | | 1 |
| 31 | 300-319 | VDVNTNELLKSEQLLTASER | | | | | | | | | | | |
| 32 | 310-329 | SEQLLTASERNLDFRDLYDP | | | | | | | | | | | |
| 33 | 320-339 | NLDFRDLYDPRDKAKLLYNN | | ▨ | | ▨ | | ▨ | | | | | 3 |
| 34 | 330-349 | RDKAKLLYNNLDAFGIMDYT | | | | | | | | | | | |
| 35 | 340-359 | LDAFGIMDYTLTGKVEDNHD | | | | | | | | | | | |
| 36 | 350-369 | LTGKVEDNHDDTNRIITVYM | | | ▨ | | | | | ▨ | | ▨ | 3 |
| 37 | 360-379 | DINRIITVYMGKRPEGENAS | | | | | | | | | | | |
| 38 | 370-389 | GKRPEGENASYHLAYDKDRY | | | | | ▨ | | | | | | 1 |
| 39 | 380-399 | YHLAYDKDRYTEEEREVYSY | ▨ | ▨ | | | | | ▨ | ▨ | ▨ | ▨ | 6 |
| 40 | 390-409 | TEEEREVYSYLRYTGTPIPD | | | | ▨ | | ▨ | ▨ | ▨ | ▨ | | 5 |
| 41 | 395-414 | EVYSYLRYTGTPIPDNPNDK | | | | | | | | | ▨ | | 1 |
| | | $N_2$ | 2 | 8 | 8 | 10 | 5 | 5 | 6 | 9 | 4 | 4 | |

STREPTOKINASE MUTANTS

The present invention is related to the field of biotechnology and genetic engineering techniques, particularly to a method for obtaining mutants from streptokinase, to the molecules obtained from this method, as well as the expression vectors and microorganisms for recombinant obtaining.

The streptokinase is a polypeptide of 414 amino acids residues. This is an extracellular protein produced by various strains of beta haemolytic streptococci, with molecular weight about 47.000 dalton and is a potent activator of the fibrinolytic enzyme system in humans (Tillet, W. S. and Garner, R. L. (1933) Exp. Med. 58, 485–502; Tillet, W. S.; Edwards, E. D. and Garner, R. L (1934) J. Clin. Invest 13, 47–78).

Unlike other plasminogen activators, streptokinase does not possess the intrinsic protease activity necessary to activate plasminogen to plasmin. Streptokinase activates plasminogen by the formation of 1:1 molar complex of streptokinase-plasminogen, which serves as the activator of free plasminogen to form plasmin (Schick, L. A. and Castellino, F. J. (1974) Biochem. Biophys. Res. Commun. 57, 47–54).

Streptokinase, urokinase and tissue-type plasminogen activator are at present used as thrombolytic agents in the treatment of disorders which collectively represent one of the greatest causes of death in the world, such as myocardial infarct, pulmonary thromboembolism, surgical complications and other cases of thrombosis.

The streptokinase is a bacterial protein and therefore, antigenic in humans. Antibodies to streptokinase are found in most individuals as a result of recurrent streptococcal infection (Tillet, W. S. and Garner, R. L. (1934) J. Clin. Invest. 13, 47–78). These antibodies are harmful for the use of streptokinase as thrombolytic, because high antibodies titers might neutralize streptokinase activity preventing effective thrombolysis (Urdahl, K. B.; Mathews, J. D.; Currie, B. (1996) Australian and New Zealand J. Med. 26, 49–53; Spottl, F. and Kaiser, R. (1974) Thromb. Diath. Haemorrh.32, 608). Patients are also immunized with streptokinase as a result of thrombolytic therapy and anti-streptokinase antibody titers exponentially rise post-treatment. These high anti-streptokinase antibody titers could neutralize a standard dose of streptokinase if it is administered a second time in therapy (Rao, A. K.; Pratt, C.; Berke, A.; Jaffe, A.; Ockene, L.; Schreiber, T. L.; Bell, W. R.; Knaterund, G.; Robertson, T. L. and Terrin, M. L. (1988) J. Am. Coll. Cardiol. 11,1). One of the most common side effects of streptokinase therapy are allergic reactions, which have been noted in up to 15% of treated patients (McGrath, K. G.; Zeffren, B.; Alexander, J.; Kaplan, K. and Patterson, R. (1985) J. Allergy Clin. Immunol. 76, 453; Sorber, W. A. and Herbst, V. (1988) Cutis 42, 57; Davies, K. A.; Mathieson, P.; Winearis, C. G.; Rees, A. J.; and Walport, M. J. (1990) Clin.Exp.Immunol.80, 83; Schweitzer, D. H.; Van der Wall, E. E.; Bosker, H. A.; Scheffer, E. and Macfarlane, J. D. (1991) Cardiology 78, 68; Bruserund, O. L.; Sollid, L. and Foyn-Jorgensen, P. (1986) J. Clin. Lab. Immun. 20, 69–74). The streptokinase also induces a strong cellular immune response (Bruserund, O. (1990) APMIS 98, 1077–1084; Bruserund, O.; Elsayed, S. and Pawelec, G. (1992) Mol. Immunol. 29,1097–1104; Youkeles, L. H.; Solirnan, M. Y. and Rosenstreich, D. L. (1991) J. Allergy Clin. Immunol. 88, 166–171; Randall, K.; Gelfond, D. H.; Stoffel, S.; Scharf, S.; Higuchi, R.; Horn, G. T.; Mullis, K. B. and Erlich, H. A. (1988) Science 239, 487–491).

The widespread use of streptokinase in humans makes its antigenicity an important clinical problem.

Despite the rich clinical information about the immunogenicity of streptokinase, little is known about the structural basis for its antigenicity. There is no X ray crystallographic data on the structure of streptokinase and it is not known whether certain regions of the molecule are more immunogenic than others, nor have there been studies of the molecular mechanisms responsible for antibody-mediated neutralization of streptokinase activity.

Previous reports have shown different antigenic regions in streptokinase mapped with murine anti-streptokinase monoclonal antibodies, soluble recombinant streptokinase fragment and anti streptokinase antibodies from human sera from patients treated with streptokinase (Reed, G. L.; Kussie, P. and Parhami-Seren, B. (1993) J. Immunol. 150, 4407–4415; Parhami-Seren, B.; Lynch, M.; White, H. D. and Reed, G. L. (1995) Mol. Immunol. 32, 717–724; Parhami-Seren, B.; Keel, T. and Reed, G. L. (1996) Hybridoma 15, 169–176; Gonzalezgronow, M.; Enghild, J. J.; Pizzo, S. V. (1993) Biochimica et Biophysica Acta 1180, 283–288; U.S. Pat. No. 5,240,845).

The object of the present invention is to achieve streptokinase mutants from modifications of skc-2 gene previously described (European Patent No. EP 0 489 201 B1; Estrada et al (1992) Biotechnology 10, 1138–1142) and coding for streptokinase SKC-2 (Heberkinase®, Heber Biotec SA, Havana, Cuba), such that the obtained mutants conserve their capacity for plasminogen activator complex formation and having reduced antigenicity that could constitute a preferred alternatives to native streptokinase for thrombolytic therapy. Heberkinase® contains a recombinant SKC-2 obtained after the expression of the skc-2 gene in *E. coli* (European Patent No. EP 0 489 201 B1; Estrada et al (1992) Biotechnology 10, 1138–1142).

The present invention relates to the mapping of antigenic regions located on SKC-2 using cellulose-bound peptide scans and human total sera from patients treated with Heberkinase®.

The present invention also relates to the immunological features of a synthetic 42 amino acids peptide resembling amino acids 373–414 from the SKC-2 C-terminal region using a panel of sera collected from patients before and after Heberkinase® therapy and tested in anti-SKC-2(373–414) peptide ELISA and SKC-2 (373–414) direct binding assay.

The present invention relates to a method for the cloning and expression of SKC-2 mutants corresponding to the fragments 40–1245 and 1–1119 from the skc-2 gene, which codes for SKC-2, previously described in the European Patent No. EP 0 489 201 B1, which products are proteins presenting:

a deletion of the first 13 amino acids residues at the N-terminal region, called SKC-2-N 13, which sequence corresponds to the Seq. Ident. No. 1.

a deletion of the first 13 amino acids residues at the N-terminal region with Asp-Ile-Val-Asp-Gly-Gly-6xHis tail fused at the C-terminus of the protein, called SKC-2-N13-Asp-Ile-Val-Asp-Gly-Gly-6xHis which sequence corresponds to the Seq. Ident. No. 2.

A deletion of the last 42 amino acids residues at the C-terminal region from position 373 to 414, called SKC-2-C42, which sequence corresponds to the Seq. Ident. No. 3.

A deletion of the last 42 amino acids residues at the C-terminal region from position 373 to 414 with Asp-Ile-Val-Asp-Gly-Gly-6xHis tail fused at the C-terminus of the protein, called SKC-2-C42-Asp-Ile-Val-Asp-Gly-Gly-6xHis, which sequence corresponds to the Seq. Ident. No. 4.

The present invention also relates to these mutant proteins, which molecular weight is 46.000 dalton for SKC-2-N13, 47.000 dalton for SKC-2-N13-Asp-Ile-Val-Asp-Gly-Gly-6xHis, 42,000 dalton for SKC-2-C42 and 43.000 dalton for SKC-2-C42-Asp-Ile-Val-Asp-Gly-Gly-6xHis, which amino acids sequences corresponds to the Seq. Ident. No. 1–4. The fragments of nucleotide sequence from skc-2 gene were obtained from pEKG3 plasmid (european patent No. .EP 0 489 201 B1), by genetic amplification using the polymerase chain reaction (PCR) with 6 synthetic oligonucleotides denominated sk1, sk2, sk3, sk4, sk5 and sk6, having sequences identified with the Seq. Ident. No. 5–10.

The present invention also relates to recombinant DNA including the nucleotide fragments 40–1245 and 1–1119 from skc-2 gene, such as vectors pEMI-1 (FIG. 2), pSKH-11 (FIG. 3), pIJ-4 (FIG. 4) and pMC-8 (FIG. 5) for the expression of these fragments in bacteria. For expression in *E. coli* these fragments were cloned under the tryptophan promoter and with the transcription termination signal from phage T4. pSKH-11 and pMC8 vectors also having a coding sequence for the Asp-Ile-Val-Asp-Gly-Gly-6xHis amino acids fused at the 3' end from the respective DNA fragments and translation termination codon TAA.

The present invention relates to the microorganisms resulting from transformation of *E. coli* strain W 3110 with vectors pEMI-1, pSKH-11, pIJ4 and pMC8. The transformants *E. coli* clones were called WSK-N13, WSK-N13-H, WSK-C42 and WSK-C42-H respectively.

Another aspect of this method is the possibility to express the DNA fragments 40–1245 and 1–1119 from skc-2 gene in bacteria, reaching high levels of expression, around 350 mg/l from both mutant proteins, which were called mut-N13 and mut-C42, respectively.

The method described in the present invention, given the expression levels obtained for these products, makes it possible to reach optimum purity thereof for its administration to human beings and animals, without the need to develop a complex and expensive purification process. The present invention relates to biological activity of mutant protein mut-N13, which showed a dramatically diminution of their activity and of mut-C42, which conserved similar activity as native protein.

The present invention also relates to the mutant proteins mut-N13 and mut-C42, which present reduced antigenicity with respect to the native SKC-2 protein. These mutant proteins were subjected to evaluation of their antigenicity in a direct binding assay and competition experiment between mutant and native proteins, using human sera collected from patients after Heberkinase® treatment.

The present invention also relates to the mut-C42 activity which, when compared to the SKC-2 activity, was less afected by SKC-2 neutralizing antibodies present in sera from 15 patients treated with Heberkinase®, which was evidenced by "in vitro" neutralizing assay. The present invention relates to the slightly lower anti-SKC-2 antibodies generation in monkeys treated with mut-C42 in comparison with those treated with the native protein SKC-2.

The present invention relates to the neutralizing capacity developed by monkeys treated with SKC-2, which was significantly higher against SKC-2 than against mut-C42, indicating that the 42 C-terminal residues of SKC-2 contain one or more important epitopes for induction of neutralizing antibodies.

EXAMPLES

Example 1

Study of SKC-2 Antigenic Regions

To identify the regions of SKC-2 involved in anti-SKC-2 antibodies binding, the peptide spot synthesis approach as previously described by Frank, R. (1992) Tetrahedron 48, 9217–9232 was used. A cellulose-bound set of 41 overlapping 20-mer peptides (10 overlapping amino acids) spanning the primary sequence of SKC-2 (amino acids 1–414) (European paten No. EP 0 489 201 B1; Estrada et al (1992) Biotechnology 10, 1138–1142) was elaborated. The cellulose sheet was probed with human sera collected from ten patients at 10 days after Heberkinase® therapy. Cellulose sheet was soaked in ethanol to prevent possible hydrophobic interactions between the peptides. Ethanol was exchanged against Tris-buffered saline (TBS) (10 mM Tris, pH 7.6, 150 mM NaCl) by sequential washing, and nonspecific binding was blocked by incubating overnight in 10 ml of T-TBS blocking buffer (0.05% Tween 20 in TBS). The sheet was subsequently incubated for 3 h at room temperature with serum samples obtained from ten patients 10 days after Heberkinase® therapy, diluted in 10 ml of T-TBS blocking buffer. Serum samples were diluted according to the predetermined anti-SKC-2 Ab titers. Sera with $5\times10^5$, $10^5$ and $5\times10^4$ Ab titers, were diluted 1:1000, 1:500 and 1:300, respectively. Cellulose sheets were washed three times with T-TBS. Then, an alkaline phosphatase-conjugated anti-human Ab (Sigma) was added at 1:2500 dilution in T-TBS blocking buffer for 2 h. Sheets were washed three times with T-TBS. Detection of bound anti-SKC-2 Abs was achieved by incubating the sheets with 0.3 mg/ml 5-Bromo 4-chloro 3-Indolyl Phosphate (BCIP) (Sigma), 4.5 mg/ml 3-(4,5-Dimethylthiazol-2-yl)-2,5-diphenyl-tetrazolium bromide (MTT) (Sigma) in substrate buffer (100 mM Tris, pH 8.9, 100 mM NaCl, 2 mM $MgCl_2$). Positive spots developed a violet color. Washing with PBS stopped staining. Cellulose sheets carrying the peptides were finally regenerated for the next test.

Several distinct binding areas were observed for the ten tested sera (FIG. 1). However, there are in the SKC-2 molecule binding sequences that are common for most of the patients. Eight out of ten sera recognized spot 14 comprising amino acids 130–149. Seventy percent of patients recognized spot 18 comprising residues 170–189. Six out of ten samples bound at spot 1 comprising amino acids 1–20 of the SKC-2 N-terminal region. Other six patients recognized spot 39 comprising residues 380–399. Fifty percent of tested sera recognized spot 40 comprising amino acids 390–409 within the C-terminal region.

The simultaneous recognition of the spots 6 and 7 indicates the presence of a continuous epitope comprised between residues 60–69 (SKPFATDSGA). Likewise, for spots 39 and 40, the existence of a continuous epitope comprising residues 390–399 (TEEEREVYSY) was delineated. The recognition of spots 27, 28 and 29 indicated the presence of one or more continuous epitopes comprised between residues 270–289 (ISEKYYVLKKGEKPYDPFDR). Spots showing isolated positive signals, without recognition of adjacent positions, suggested the existence of continuous epitopes including more than ten amino acids.

Example 2

Study of Immunodominance of the SKC-2 C-terminal Region a) Anti-SKC-2(373–414) Peptide ELISA with Patients Sera Human total sera collected from 64 patients in different hospitals in Havana, Cuba, before (A) and ten days after (B)

Heberkinase® therapy were tested in an anti-SKC-2 ELISA. Samples before therapy showed anti-SKC-2 Ab titers between 1:10 and 1:10$^4$, while after therapy Ab titer range increased to 1:10$^3$–1:5×10$^5$. These samples were assayed in an anti-SKC-2(373–414) peptide ELISA in order to Assess the recognition rate for the C-terminal region of SKC-2. In order to know the immunodominance of SKC-2 C-terminus, a peptide corresponding to the sequence 373–414 of SKC-2, containing 42 amino acid residues (PEGENASYHLAYDKDRYTEEEREVYSYLRYTG TPIPDNPNDK) was synthesized. Polyvinyl plates (High Binding, Costar, Cambridge, Mass., U.S.A.). Plates were coated with 1 µg/ml SKC-2(373–414) peptide, and incubated overnight at 4° C. After washing three times with PBS-Tween, plates were blocked using 2% bovine serum albumin (BSA) (Sigma), and 100 µl of 1:50 dilution of each human serum were added. The binding of human Abs to SKC-2(373–414) peptide was measured using a horseradish peroxidase-conjugated anti-human Ab (Sigma). The reaction was developed using 100 µl per well of 1 mg/ml o-phenylenediamine (Sigma), 0.03% H$_2$O$_2$ in substrate buffer (0.1M citric acid, 0.2M Na$_2$HPO$_4$, pH 5.0). After 30 min, the reaction was stopped with 50 µl of 4M H$_2$SO$_4$. Results were measured on a Multiskan system (Titertek, Helsinki, Finland) at 492 nm. Each sample was tested by duplicated. Different degrees were considered for positive samples according to the sample/background ratio: Samples showing absorbance values two, three and four or more times higher than the background were classified as +, ++ and +++, respectively. The results are shown in the Table 1. Before therapy (A), 39% of patients recognized the SKC-2 (373–414) peptide. As it was expected, the recognition increased to 64% after therapy (B). This increase was not only due to a larger number of positive samples, but also to higher intensity of these positive signals.

TABLE 1

Anti-SKC-2(373-414) peptide ELISA with patient sera.

| Patient | A | B |
|---|---|---|
| SA 01 | + | +++ |
| SA 03 | + | + |
| SA 05 | + | ++ |
| SA 06 | − | + |
| SA 07 | − | + |
| SA 08 | − | − |
| SA 09 | − | + |
| SA 10 | − | + |
| SA 11 | − | ++ |
| SA 12 | ++ | +++ |
| SA 13 | + | +++ |
| SA 14 | − | ++ |
| SA 15 | + | − |
| SA 17 | + | + |
| SA 18 | − | − |
| SA 19 | − | − |
| SA 20 | + | +++ |
| SA 23 | − | − |
| SA 24 | − | ++ |
| SA 25 | − | − |
| SA 26 | − | − |
| SA 28 | + | +++ |
| SA 29 | + | − |
| SA 30 | + | +++ |
| SA 31 | − | +++ |
| SA 32 | + | +++ |
| SA 33 | + | +++ |
| SA 34 | + | +++ |
| SA 35 | − | + |
| SA 37 | + | − |
| SA 39 | − | − |
| SA 40 | + | ++ |
| SA 41 | − | +++ |
| SA 42 | − | − |
| SA 45 | − | +++ |
| SA 46 | − | − |
| SA 47 | ++ | + |
| SA 48 | + | ++ |
| SA 49 | − | + |
| SA 50 | − | +++ |
| SA 51 | + | − |
| SA 52 | − | +++ |
| SA 53 | − | +++ |
| SA 54 | − | +++ |
| SA 55 | − | +++ |
| SA 56 | − | − |
| SA 58 | + | ++ |
| SA 59 | + | − |
| SA 60 | − | ++ |
| SA 61 | − | − |
| SA 64 | − | ++ |
| SA 65 | − | − |
| EC 04 | − | ++ |
| EC 05 | ++ | + |
| EC 06 | − | + |
| EC 10 | − | + |
| EC 23 | ++ | − |
| EC 25 | − | − |
| CG 05 | + | +++ |
| CG 06 | − | − |
| CG 07 | +++ | +++ |
| CG 10 | − | − |
| LD 01 | − | − |
| LD 03 | − | − |
| Total | 64 | 64 |
| (+) | 25 | 41 |
| %(+) | 39.063 | 64.063 | b) SKC-2(373–414) Direct Binding Assay with Patients Sera

In order to asses the proportion of the anti-SKC-2 (373–414) recognition with respect to the total anti-SKC-2 Ab response, we performed a direct binding assay with 21 out of 64 patient sera obtained after Heberkinase® therapy. Experimental conditions were determined by titration of samples against native SKC-2 and SKC-2(373–414) peptide in order to select those dilution conditions (dln.1 for SKC-2(373–414) and dln.2 for SKC-2) in which there is not excess of Ab directed to each molecule.

Polyvinyl plates (High Binding, Costar, Cambridge, Mass., U.S.A.) Plates were divided in two sections and coated with 10 µg/ml SKC-2 and 1 µg/ml SKC-2(373–414) peptide, respectively. After washing three times with PBS-Tween, plates were blocked with 2% BSA. One hundred µl of human sera collected from patients ten days after Heberkinase® therapy were added at previously determined optimal dilutions. After incubation for 1 h at 37° C., the binding of human anti-SKC-2 Abs to molecules on solid phase was measured using a horseradish peroxidase-conjugated anti-human Ab (Sigma). The reaction was developed using 100 µl per well of 1 mg/ml o-phenylenediamine (Sigma), 0.03% H$_2$O$_2$ in substrate buffer (0.1M citric acid, 0.2M Na$_2$HPO$_4$, pH 5.0). After 30 min, the reaction was stopped with 50 µl of 4M H$_2$SO$_4$. Results were measured on a Multiskan system (Titertek, Helsinki, Finland) at 492 nm. Each sample was tested by duplicated. Percent direct binding of human anti-SKC-2 Abs to SKC-2(373–414) peptide was determined from the following formula:

$$100 \times \frac{(\text{Absorbance binding to SKC-2(373-414)}) \times \text{dln.1}}{(\text{Absorbance binding to SKC-2}) \times \text{dln.2}}$$

Percent Ab binding to SKC-2(373–414) ranged between 0.14 and 10.68% with respect to anti-SKC-2 Ab recognition (Table 2). The mean value from 21 samples was 2.96% (St. dev.=3.30).

TABLE 2

SKC-2(373–414) direct binding assay with patient sera

| Patient | SKC-2 | | | SKC-2(373-414) | | | % Direct Binding |
|---------|------------|-------------------|------------------|------------|-------------------|------------------|------------------|
|         | Absorbance | dilution factor | Abs × dilution | Absorbance | dilution factor | Abs × dilution |  |
| SA 01 | 0.239 | 6400 | 1528.53 | 0.255 | 160 | 40.77 | 2.67 |
| SA 11 | 0.290 | 12800 | 3709.87 | 0.267 | 20 | 5.35 | 0.14 |
| SA 12 | 0.244 | 3200 | 781.87 | 0.284 | 80 | 22.75 | 2.91 |
| SA 13 | 0.260 | 6400 | 1662.93 | 0.289 | 80 | 23.11 | 1.39 |
| SA 20 | 0.232 | 6400 | 1486.93 | 0.265 | 40 | 10.59 | 0.71 |
| SA 24 | 0.267 | 6400 | 1707.73 | 0.233 | 20 | 4.66 | 0.27 |
| SA 28 | 0.272 | 12800 | 3479.47 | 0.292 | 320 | 93.55 | 2.69 |
| SA 30 | 0.259 | 6400 | 1656.53 | 0.283 | 80 | 22.67 | 1.37 |
| SA 31 | 0.228 | 12800 | 2922.67 | 0.230 | 80 | 18.43 | 0.63 |
| SA 32 | 0.251 | 6400 | 1608.53 | 0.268 | 20 | 5.37 | 0.33 |
| SA 33 | 0.304 | 12800 | 3889.07 | 0.290 | 1280 | 370.99 | 9.54 |
| SA 34 | 0.263 | 12800 | 3370.67 | 0.279 | 320 | 89.23 | 2.65 |
| SA 41 | 0.262 | 12800 | 3351.47 | 0.265 | 80 | 21.23 | 0.63 |
| SA 45 | 0.236 | 6400 | 1512.53 | 0.252 | 640 | 161.49 | 10.68 |
| SA 50 | 0.243 | 12800 | 3108.27 | 0.289 | 80 | 23.11 | 0.74 |
| SA 52 | 0.311 | 12800 | 3985.07 | 0.298 | 320 | 95.47 | 2.40 |
| SA 53 | 0.297 | 12800 | 3799.47 | 0.274 | 40 | 10.95 | 0.29 |
| SA 54 | 0.256 | 12800 | 3274.67 | 0.256 | 1280 | 327.47 | 10.00 |
| SA 55 | 0.221 | 3200 | 706.67 | 0.284 | 80 | 22.75 | 3.22 |
| CG 05 | 0.242 | 6400 | 1547.73 | 0.280 | 160 | 44.77 | 2.89 |
| CG 07 | 0.223 | 800 | 178.27 | 0.267 | 40 | 10.67 | 5.99 |
|  |  |  |  |  |  | Total | 21 |
|  |  |  |  |  |  | Mean | 2.96 |
|  |  |  |  |  |  | St.Dev. | 3.30 | c) Study of the Recognition of SKC-2(373–414) Peptide by Sera from Normal Donors Antibodies directed against streptokinase are found in most individuals as a result of recurrent streptococcal infections. Regarding the immunodominance of SKC-2 C-terminal region, part of this antibody response is likely to direct against amino acids 373–414 from the C-terminus of the molecule. In order to assess the proportion of this recognition in normal population, 1008 normal donor sera were tested using an anti-SKC-2(373–414) peptide Ultra-Micro-ELISA. Plates (Greiner, Frankfurt, Germany) were coated with 15 $\mu$L per well of 2 $\mu$g/mL SKC-2(373–414) in coating buffer (50 mM $Na_2CO_3$, 50 mM $NaHCO_3$, pH 9.6), and incubated at 37° C. for 4 h. After washing with Tris-buffered saline, 0.05% Tween 20 (TBS-Tween), plates were blocked with 2% BSA (Sigma) at room temperature, overnight. Blocking solution was removed and plates were dried at 37° C. for 1 h. Ten $\mu$L of 1:20 dilution of each human serum in TBS, 0.05% Tween 20, 1% BSA were added. Plates were incubated at 37° C. for 30 min and washed four times. Binding of human Abs to SKC-2(373–414) peptide was measured using 1:5000 dilution of an alkaline phosphatase-conjugated anti-human IgGAb (Sigma). Plates were incubated at 37° C. for 30 min and washed four times. Reactions were developed by addition of 10 $\mu$L per well of substrate solution (0.13 mg/mL 4-methylumbelliferyl phosphate in 3M diethanolamine-HCl buffer, pH 9.8) and plates were incubated at room temperature for 30 min. Fluorescence was measured using an Ultra-Micro-ELISA plates reader PR-521 (SUMA Technology, Havana, Cuba). Each sample was tested by duplicated. The experiment was validated by positive, negative and blank controls. In order to homogenize the results, the sample/positive control ratio was determined for each tested serum using the following formula:

$$\text{Sample/Positive} = \frac{(\text{Sample fluorescence}) - (\text{Blank fluorescence})}{(\text{Positive control fluorescence}) - (\text{Blank fluorescence})}$$

Sample/Positive ratio of the 1008 tested samples ranged between 0.005 and 1.970. The mean value was 0.369 (St. Dev. 0.499). A frequency distribution was made according to 40 classes defined by Sample/Positive ratio (FIG. 2).

Figure 3:
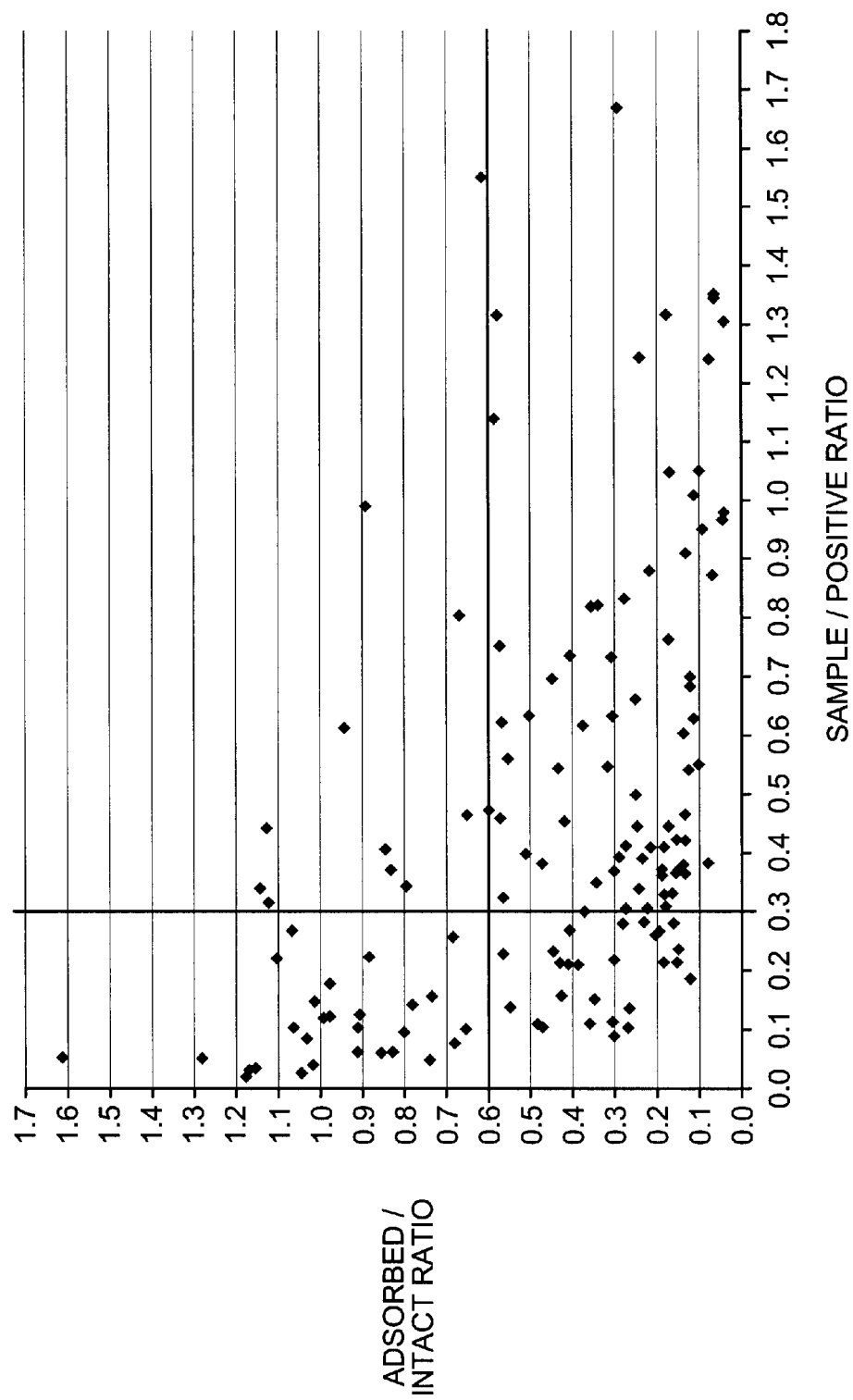

In order to determine the cut off for the assay an auxiliary experiment was performed. Inhibition of anti-SKC-2 (373–414) Ab binding by previous adsorption of samples with the same peptide was studied. This experiment was performed with 140 samples randomly selected from 1008 previously tested. A 1:4 dilution of each sample was mixed with SKC-2(373–414) peptide at a final concentration of 5 $\mu$g/mL and incubated at room temperature with agitation, overnight. Samples were centrifuged at 12000 rpm for 10 min in order to precipitate immunocomplexes. Plates were coated with 2 $\mu$g/mL SKC-2(373–414), as described above. Adsorbed samples were diluted 1:5 to reach 1:20 final dilution. Each one was accompanied by 1:20 dilution of intact serum as a control. Plates were incubated at 37° C. for 30 min and washed four times. Next steps were performed as described above. Each sample was tested by duplicated. The proportion of each adsorbed sample with respect to its intact control (Adsorbed/Intact) was determined. Positive sample was considered when Adsorbed/Intact ratio was no higher than 0.6. FIG. 3 shows plots of Adsorbed/Intact ratio versus Sample/Positive ratio. For small Sample/Positive ratio values there is a high concentration of samples over 0.6. However, as this ratio increases, negative samples decrease. Based on these results a Sample/Positive ratio value of 0.3 was selected as cut off because it assures to take the highest number of positive individuals with a minimum unespecificity.

Figure 4:
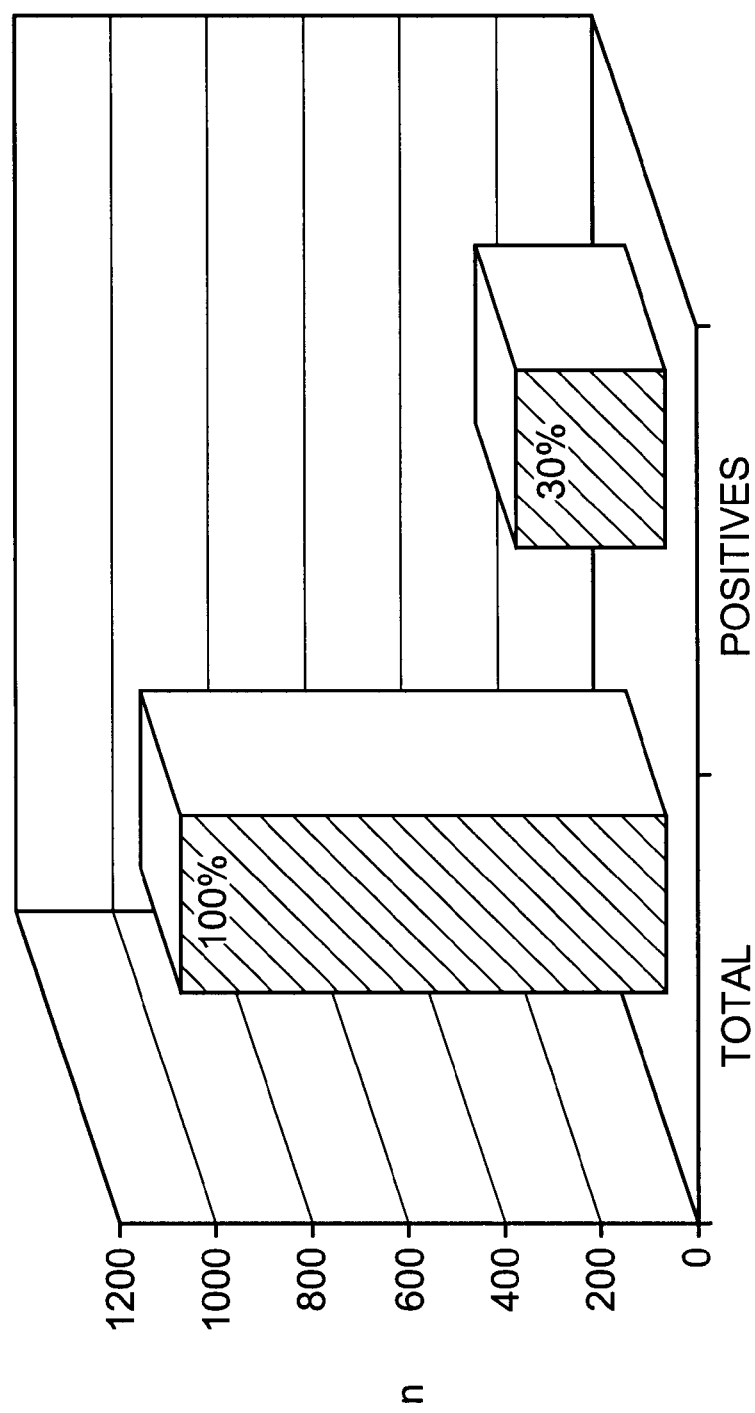
Figure 5:
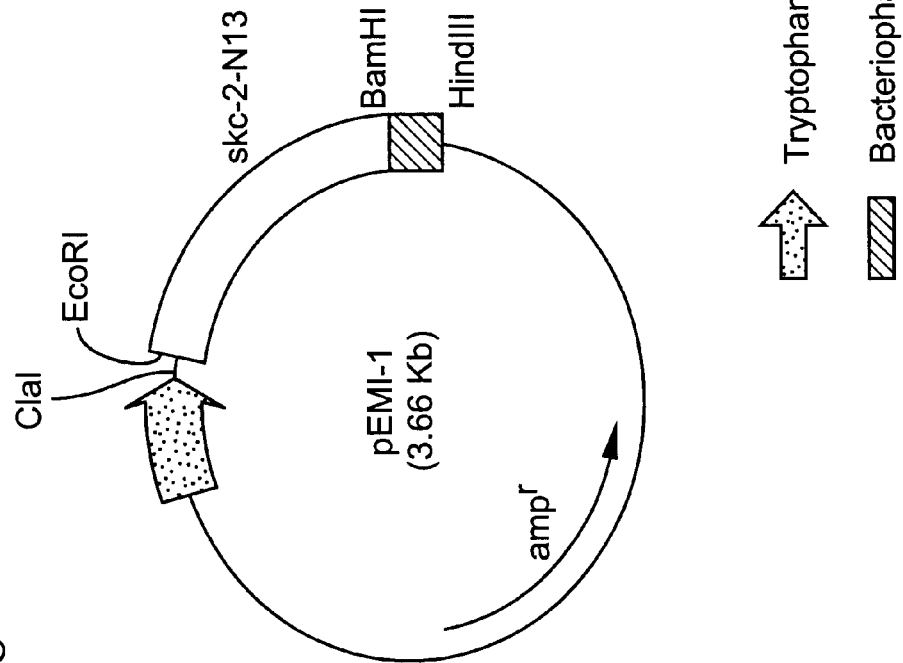
Figure 6:
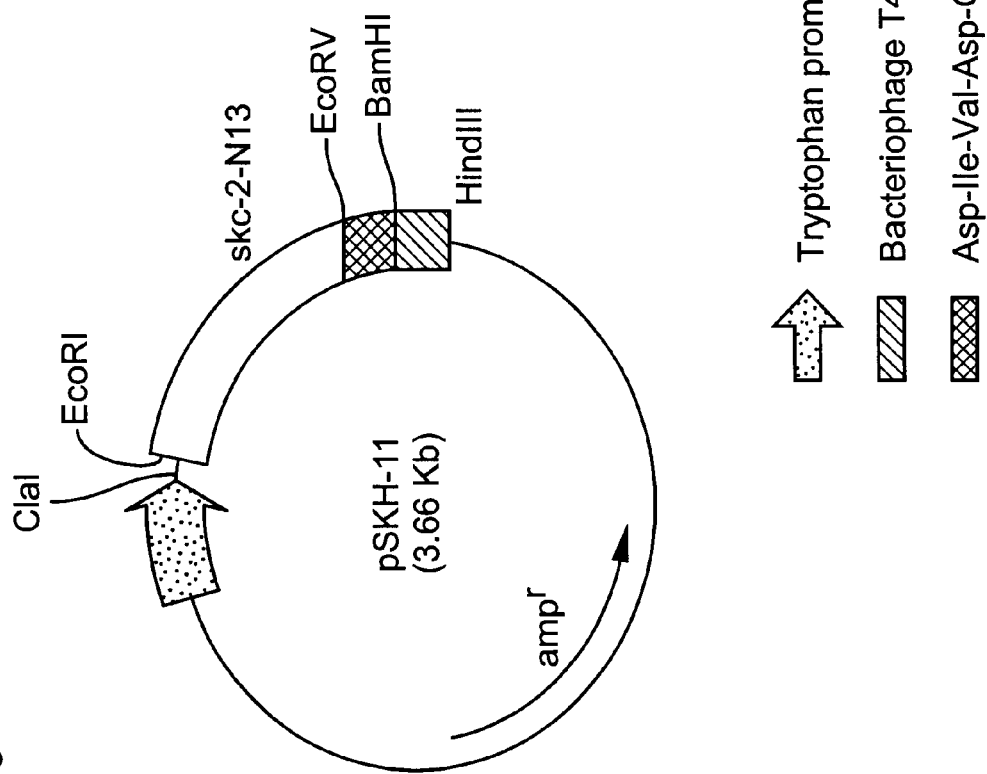
Figure 7:
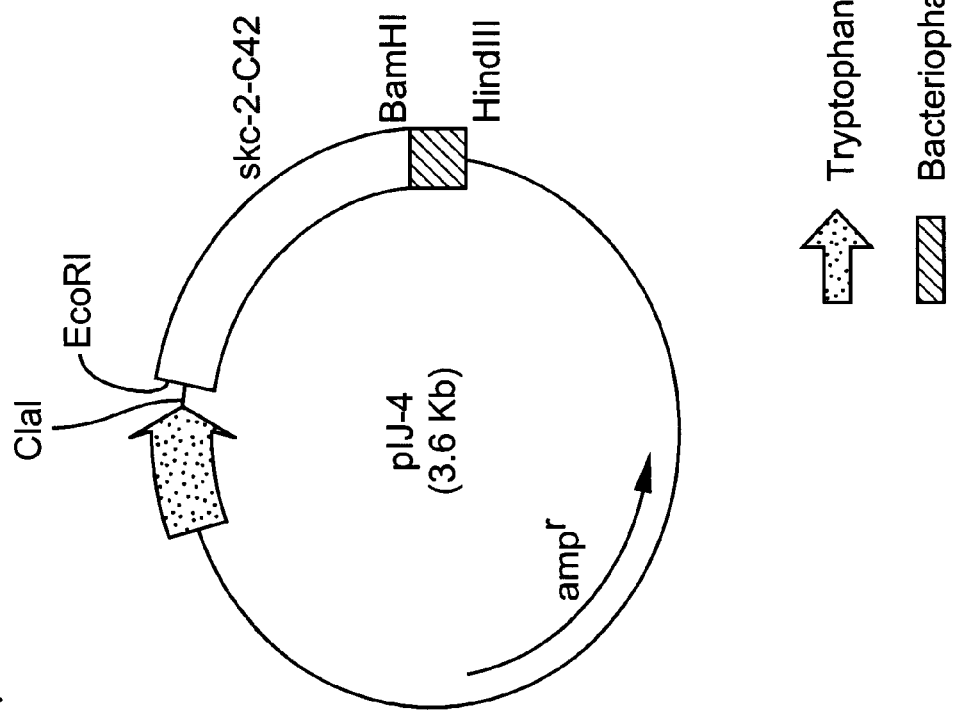
Figure 8:
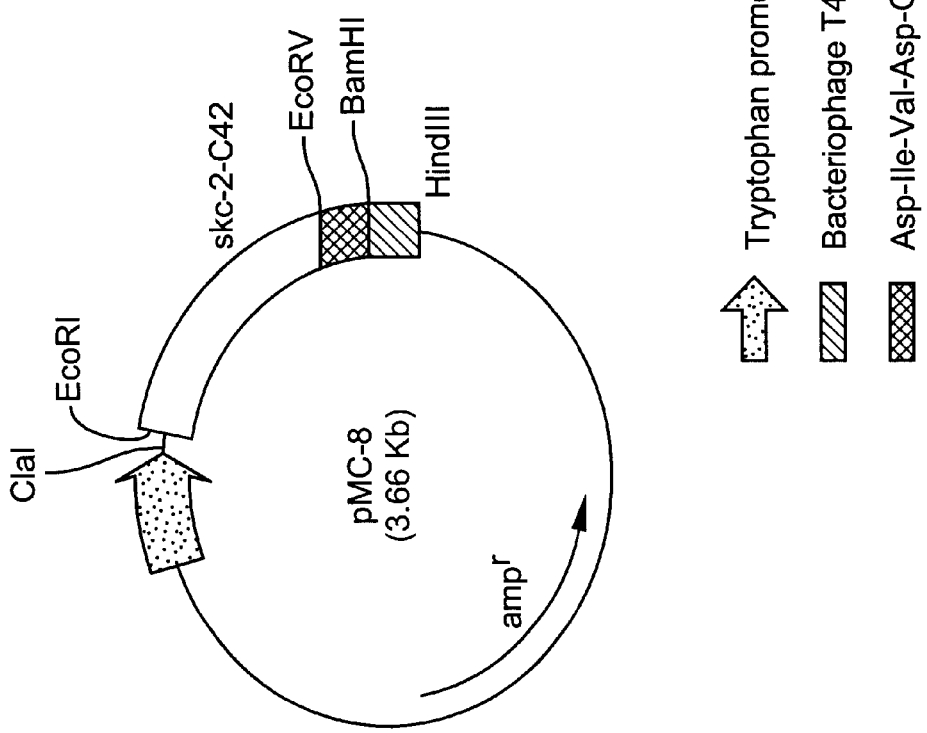

Regarding a cut off of 0.3, the analysis of the results showed that 306 out of 1008 tested samples recognize SKC-2(373–414) peptide, representing 30.36% from total (FIG. 4).

Example 3
Cloning and Expression of SKC-2 Mutants Protein

For subcloning of skc-2 mutants in bacteria, DNA from plasmid pEKG-3 (containing skc-2 gene; European Patent No. EP 0 489 201 B1; Estrada et al (1992) Biotechnology 10, 1138–1142) was taken and the fragments were amplified by PCR using oligonucleotides sk1, sk2, sk3, sk4, sk5 and sk6. Oligonucleotides sk1 and sk4 have an EcoRI restriction site, oligonucleotides sk2 and sk5 have a BamHI restriction site, and oligonucleotides sk3 and sk6 have an EcoRV restriction site. Oligonucleotides sk1 and sk4 have an ATG codon for the translation initiation. Oligonucleotides sk2 and sk5 have a TAA codon for translation termination.

One µg of pEKG-3 was taken and the gene coding for SKC-2 was amplified by PCR (Dagert, M., and Erlich, S. L. (1974) Gene 6: 23–28) using the oligonucleotides sk1, sk2 and sk3 for cloning the mutant gene cloning with a 39 bp deletion at the 5' end, corresponding to the nucleotide fragment 40–1245 from skc-2 gene; and oligonucleotides sk4, sk5 and sk6 for the cloning mutant gene with a 126 bp deletion at the 3' end, corresponding to the nucleotide fragment 1–1119 from skc-2 gene.

For each reaction 100 pmol of each oligonucleotide, 2 units of Taq polymerase (Enzibiot) and 200 µmol of each dNTP were used. Reactions were performed in 10 mM $MgCl_2$, 100 mM dTT, 10 mM NaCl and 100 µl mineral oil. Twenty five amplification cycles were performed, wherein each one the reaction was incubated at 95° C. for 1 minute for denaturisation, at 50° C. for 45 seconds for oligonucleotide anneling at 70° C. for 80 seconds for DNA chains extension. An amplification efficacy higher than 5% was obtained.

For cloning in bacteria (*E. coli*), a genetic construct containing the trytophan promoter of *E. coli* and the termination signal of bacteriophage T4 terminator was used. Fragments amplified by PCR using combinations of primer-oligonucleotides sk1–sk2 and sk4-sk5 were digested with EcoRI and BamHI, and ligated with the EcoRI-BamHI digsted vector. Fragments amplified by PCR using combinations of primer-oligonucleotides sk1–sk3 and sk4-sk6 were digested with EcoRI and EcoRV, and ligated with the EcoRI-EcoRV digested vector containing a coding sequence for the amino acid tail Asp-Ile-Val-Asp-Gly-Gly-6xHis that was fused to the 3' end of both fragments. These constructions were transformed into a preparation of competent cells ((Hanahan, D. (1983) J. Mol. Biol. 166, 557–580) of *E. coli* strain MC1061 (F⁻ara D 139 (ara-leu) 7696 (lac) X74 gal u galk hsd R2(rk⁻mk⁺) mcrB1 rpsL (Str$^r$)), having a Frequency higher than $10^7$ transformants per DNA Mg.

Resultant colonies were applied to LB plates (10 gr/l trypton, 5 gr/l yeast extract, 10 gr/l NaCl and 50 mg/ml ampicillin), and subjected to hybridization (Maniatis, T.; Frisch, E. F. and Sambrook, J. (1982) Cold Spring Harbor Laboratory, USA), using the fragment resulting from PCR amplification as a probe, labelled with dATP$^{32}$ (Amersham, R.U.) and the Klenow fragment of DNA-polymerase I of *E. coli* for 30 minutes at 37° C. The reaction was stopped by EDTA and heat. The hibridization was performed in Whatman 541 filters, 8% of the colonies were positive clones, which were examined by restriction analysis and had the same pattern of digestion with more than 10 restriction enzymes. Moreover, positive clones were checked by double chain DNA sequencing (Sanger, F.; Nickler, S. and Coulson, A. K. (1977) Proc. Natl. Acad. Sci. USA 74, 5463–5467), using an oligonucleotide of 17 bases (5' ATCATCGAAC-TAGTAA 3') which annels at the 3' promoter end, corroborating that 39 bp deletion at the 5' end of the gene and joining to the promoter were correct; and an oligonucleotide of 22 bases (5' GGTCATTCAAAAGGTCATCCAC 3') which Anneals at the 5' end of the T4 terminator, corroborating that 126 bp deletion of at the 3' end of the gene and fusion to the coding sequence for Asp-Ile-Val-Asp-Gly-Gly-6xHis tail was correct.

The selected clones (FIGS. 5, 6, 7 and 8) were called pEMI-1 (mutant with 39 bp deletion the at the 5' end having the skc-2 gene fragment 40–1245), pSKH-11 (mutant with 39 bp deletion at the 5' end having the skc-2 gene fragment 40–1245 fused to the coding sequence for Asp-Ile-Val-Asp-Gly-Gly-6xHis tail at the 3' end), pIJ-4 (mutant with 126 bp deletion at the 3' end having the skc-2 gene fragment 1–1119) and pMC-8 (mutant with 126 bp deletion at the 3' end having the skc-2 gene fragment 1–1119 fused to the coding sequence for Asp-Ile-Val-Asp-Gly-Gly-6xHis tail at the 3' end). These clones were transformed in the *E.coli* strain W3110 and were subjected to a fermentation process, wherein stable expression levels higher than 10% of the total protein content of the cells were obtained, and 150–200 mg of SKC-2 mutants mut-N13 and mut-C42 per litre of culture medium were obtained.

Example 4
Purification of SKC-2 Mutant Proteins

*E. coli* cells were suspended in the disruption buffer that containing 50 mM Tris-HCl, 0.5M NaCl, 3 mM EDTA, pH 7.0 at a concentration of 40% (w/v) and mechanically disrupted by using a French Pressure (Ohtake, Japan). Cells were passed twice through the French Pressure in order to achieve an optimal cell disruption. Disrupted cells were homogenized and centrifuged at 15000 rpm for 1 h at 4° C. by using a RPR 20-2 rotor (Hitachi, Japan). The supernatant, containing the recombinant streptokinase, was collected for protein purification.

The supernatant was loaded into a Sephadex G-25 gel filtration column (2.6×27.5; I.D.×L., in cm) (Pharmacia, Sweden) which was previously equilibrated with 0.02M Tris-HCl pH 6.0 at a flow rate of 5 ml/min. Proteins eluted from the gel filtration support were loaded into a Q-Sepharose Fast Flow anion exchange column (2.6×5.5; I.D.×L., in cm) (Pharmacia, Sweden), previously equilibrated with 0.02M Tris-HCl pH 6.0 at a flow rate of 10 ml/min. The non-bound bound protein was washed from the column with this equilibrium buffer. Elution of proteins was carried out with a linear gradient of increasing NaCl concentrations, which was produced by using an FPLC system (Phannacia, Sweden). The recombinant streptokinase was eluted at 0.12M NaCl in the equilibrium buffer.

The pH of the eluate from the ion exchange support was increased from 6.0 to 8.0 by adding a 1M Tris solution. Ammonium sulfate was added to this sample up to 10% saturation of this salt. This sample was loaded into a column (1.6×5; I.D.×L., in cm) containing a TSK-butyl (Tosohaas Technical Center, USA) hydrophobic interaction chromatography support. This column was equilibrated with 0.02M Tris-HCl, ammonium sulfate at 10% saturation, pH 8.0, at a flow rate of 4 ml/min. After washing the non-bound protein with equilibrium buffer, the recombinant streptokinase was eluted by using an FPLC system (Pharmacia, Sweden) which produced a linear gradient of decreasing ammonium sulfate concentration in the equilibrated buffer. The recombinant streptokinase was eluted at a concentration of ammonium sulfate of 3% saturation. The material obtained was sterilized by filtration through a 0.22-$\mu$m Millipore filter.

Example 5

Determination of Biological Activity of SKC-2 Mutant Proteins

The in vitro biological activity of mutant proteins mut-N13 and mut-C42 was determined by agarose-fibrin plates assay (Astrup, T. and Mullertz, S. (1952) Arch. Biochem. Biophys 40, 346–351), chromogenic substrate (Fiberger, P. (1982) J. Clin. Lab. Invest. 42, Suppl. 162, 49–54) and clot lysis (Westtund, L. E. and Anderson, L. O. (1985) Thrombosis Research 37, 213–223). mut-C42 showed a specific activity of 50 000–100 000 IU/mg similar to that obtained for native SKC-2, and mut-N13 showed a dramatic diminution of its specific activity with values of 2000–4000 IU/mg.

mut-C42 in vivo fibrinolytic activity was verified in clinical test on animals, wherein there was success in dissolving clots in the femoral arteries of rabbits and coronary arteries of dogs. Blood parameters maintained similar to those obtained for native SKC-2 and those reported in the literature for this type of product.

Example 6

Immunological Characterization of SKC-2 Mutant Proteins. In vitro Assays a) mut-N13 and mut-C42 Direct Binding Assay by Human Anti-SKC-2 Antibodies A direct binding assay was performed in order to compare mut-N13 and mut-C42 mutant proteins with native SKC-2 regarding their capacity for binding human anti-SKC-2 Abs present in sera from patients after Heberkinasa® therapy. Polyviline plates (Medium binding, Costar, Cambridge, Mass., U.S.A) were divided in three sections and coated with 10 $\mu$g/ml of full length SKC-2, mut-N13 and mut-C42, respectively. Then, plates were washed three times with PBS-Tween. One hundred $\mu$l of human sera collected from eight patients ten days after Heberkinase® therapy were added at a previously determined optimal dilution. Samples were diluted according to the predetermined anti-SKC-2 Ab titers. For sera with $5\times10^5$, $10^5$ and $5\times10^4$ Ab titers, dilutions were of $1:3.2\times10^4$, $1:1.6\times10^4$ and $1:2\times10^3$, respectively. After incubation for 1 h at 37° C., the binding of human anti-SKC-2 Abs to molecules on solid phase was measured using a horseradish peroxidase-conjugated anti-human Ab (Sigma). The reaction was developed using 100 $\mu$l per well of 1 mg/ml o-phenylenediamine (Sigma), 0.03% $H_2O_2$ in substrate buffer (0.1M citric acid, 0.2M $Na_2HPO_4$, pH 5.0). After 30 min, the reaction was stopped with 50 $\mu$l of 4M $H_2SO_4$. Each sample was tested by duplicated. Percent direct binding of human anti-SKC-2 Abs to deletion mutants (Table 3) was determined from the following formula:

100×(Absorbance binding to mutant proteins/(Absorbance binding to SKC-2)

TABLE 3

Direct binding assay of human anti-SKC-2 antibodies to mutant proteins mut-N13 and mut-C42.

| Sera | mut-N13 | mut-C42 |
| --- | --- | --- |
| SA 06B | 86.0335 | 43.3892 |
| SA 07B | 96.0191 | 55.414 |
| SA 12B | 95.2128 | 51.0638 |
| SA 14B | 92.0415 | 55.1903 |
| SA 17B | 88.8889 | 49.537 |
| SA 28B | 88.8631 | 48.7239 |
| SA 32B | 87.8238 | 50.7772 |
| SA 42B | 84.4828 | 51.7241 |
| Mean | 89.9207 | 50.7275 |
| St. Dev. | 4.15685 | 3.82233 |
| n | 8 | 8 |
| t | 6.85822 | 36.4605 |
| P | 0.00012 | 1.5E−09 |

Figure 9:
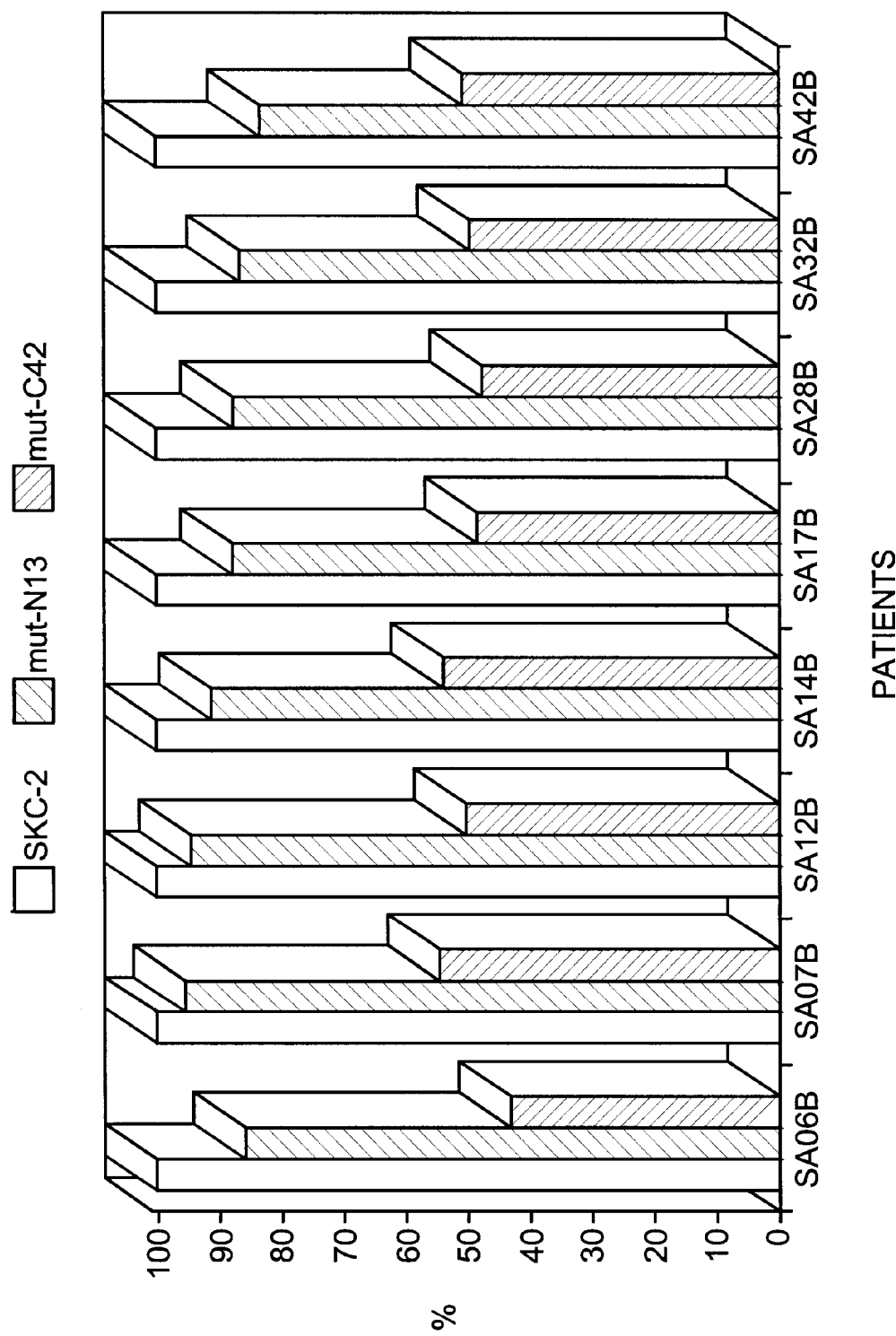

All eight tested sera showed a similar binding pattern. Binding of human anti-SKC-2 Abs to mut-N13 was 89.92% (P=0.00012) and to mut-C42 was 50.73% (P=$1.52\times10^{-9}$) of their binding to native SKC-2 (FIG. 9).

b) Competition Assay of Proteins mut-N13, mut-C42 and SKC-2

Figure 10:
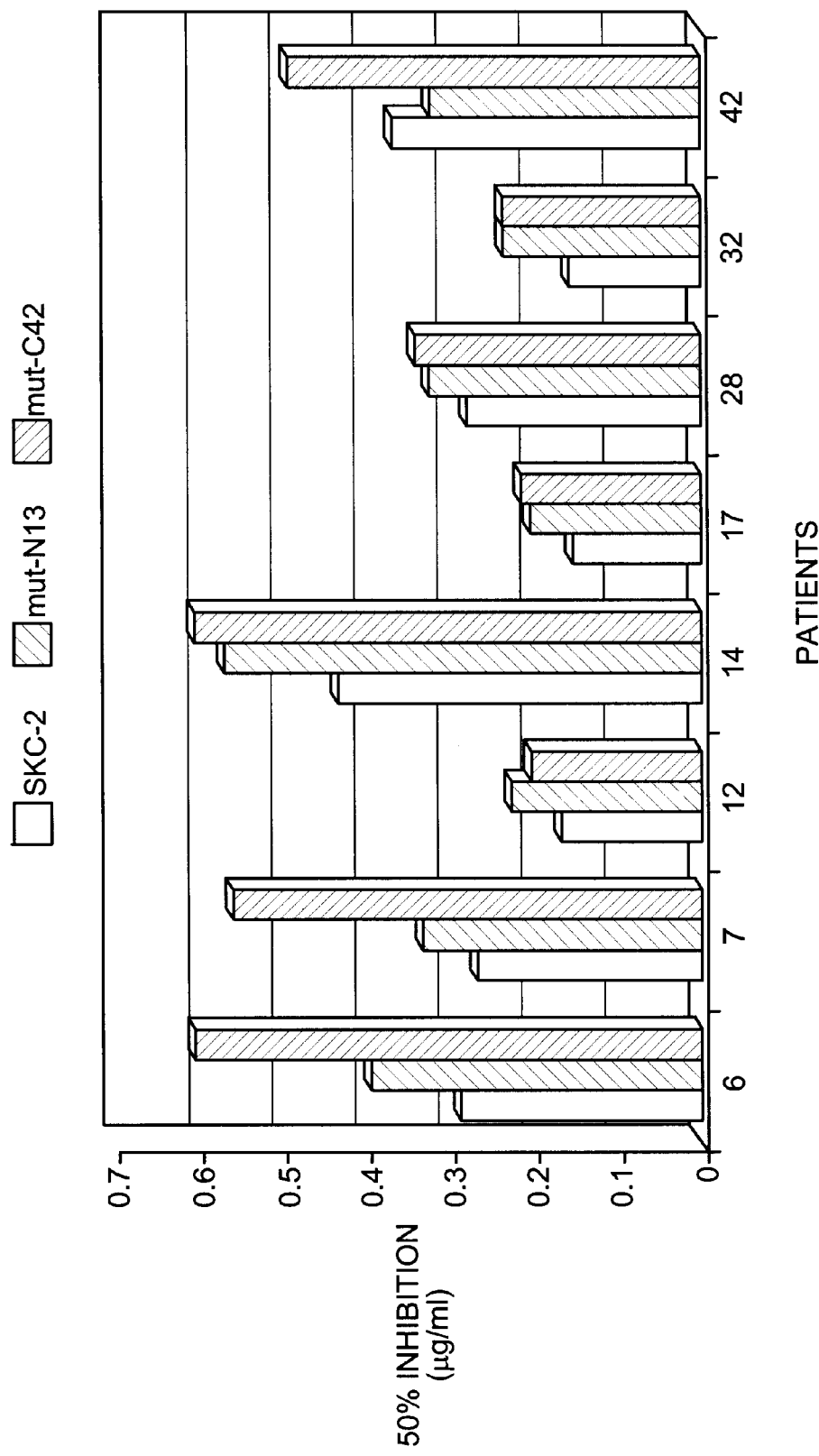
Figure 11:
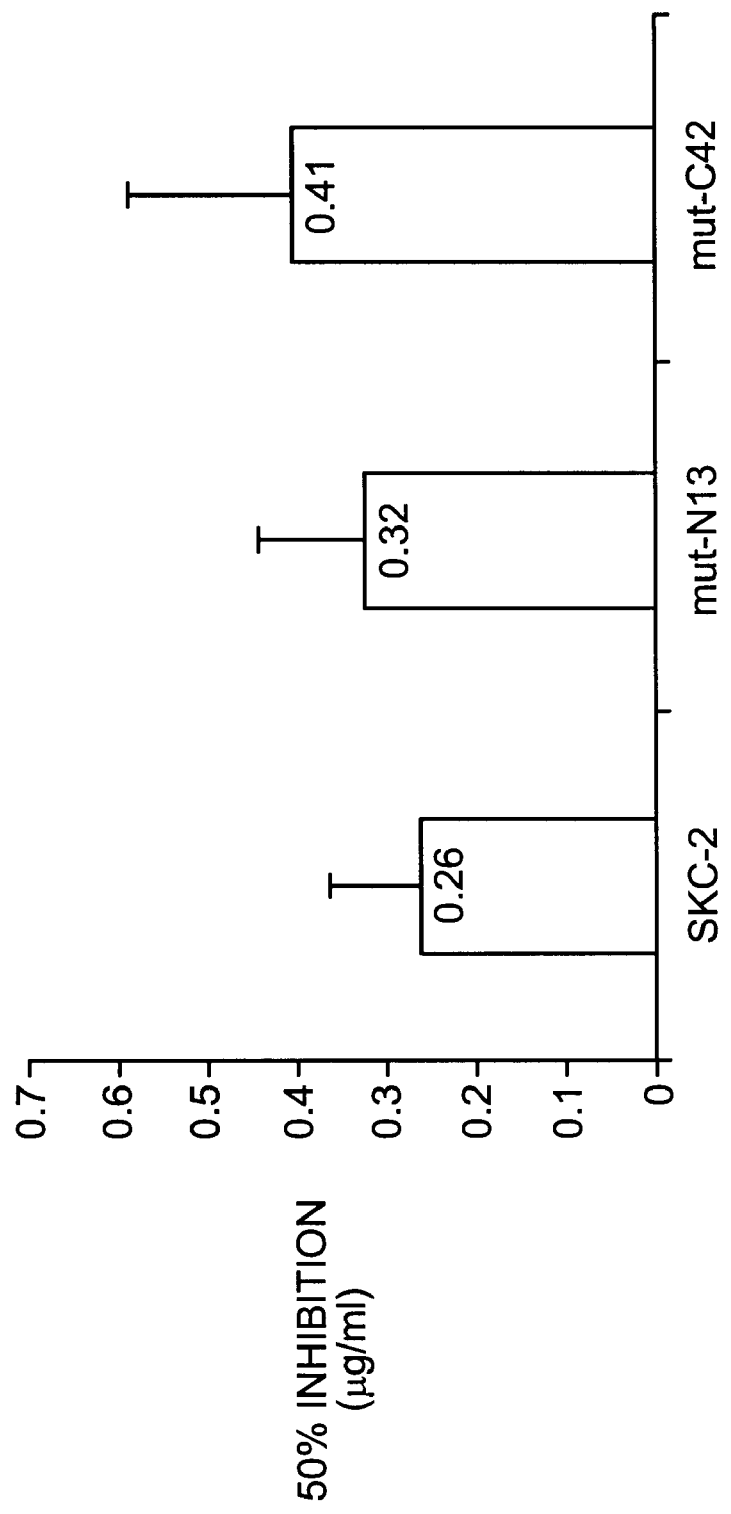

Similar results were obtained from the same eight samples using a competition assay in which native and mutant proteins mut-N13 and mut-C42 competed with a biotinylated SKC-2 for binding human anti-SKC-2 Abs. Plates (Costar) were coated with 5 $\mu$g/ml of goat anti-human Abs in coating buffer. After washing three times with PBS-Tween, plates were blocked using 2% BSA (Sigma). One hundred $\mu$l of human sera collected from eight patients ten days after Heberkinase® therapy were added at a previously determined optimal dilution. Samples were diluted according to the predetermined anti-SKC-2 Ab titers. For sera with $5\times10^5$, $10^5$ and $5\times10^4$ Ab titers, dilutions were of $1:10^4$, $1:5\times10^3$ and $1:10^3$, respectively. This way, human anti-SKC-2 Abs were immobilized on the coated plates. After washing, 100 $\mu$l of a solution of 1 $\mu$g/ml of biotinylated SKC-2 mixed with different concentrations of non-labeled full length SKC-2 or deletion mutants (4–0.25 $\mu$g/ml, two-fold dilutions) were added. The binding of biotinylated SKC-2 to human anti-SKC-2 Abs, after competition with non-labeled molecules, was measured using horseradish peroxidase-conjugated streptavidin. The reaction was developed using 100 $\mu$l per well of 1 mg/ml o-phenylenediamine (Sigma), 0.03% $H_2O_2$ in substrate buffer (0.1M citric acid, 0.2M $Na_2HPO_4$, pH 5.0). After 30 min, the reaction was stopped with 50 $\mu$l of 4M $H_2SO_4$. Each sample was tested by duplicate. The effective dose 50% (ED50) values for mutant and native proteins were determined from plots of absorbance versus concentration of non-labeled molecules using a Probit transformation in order to obtain 50% inhibition (Table 4; FIGS. 10 and 11).

TABLE 4

ED 50 inhibition ($\mu$g/mL) of SKC-2, mut-N13 and mut-C42 for each patient treated with Heberkinase ®.

| Sera | SKC-2 | mut-N13 | mut-C42 |
| --- | --- | --- | --- |
| 6 | 0.2865 | 0.39447 | 0.6079 |
| 7 | 0.2653 | 0.33091 | 0.5579 |
| 12 | 0.1625 | 0.22202 | 0.2007 |
| 14 | 0.4338 | 0.56878 | 0.6071 |
| 17 | 0.1519 | 0.20047 | 0.2136 |

TABLE 4-continued

ED 50 inhibition (μg/mL) of SKC-2, mut-N13 and mut-C42 for each patient treated with Heberkinase ®.

| Sera | SKC-2 | mut-N13 | mut-C42 |
|---|---|---|---|
| 28 | 0.2775 | 0.32181 | 0.3411 |
| 32 | 0.1556 | 0.23464 | 0.235 |
| 42 | 0.3678 | 0.32266 | 0.492 |
| Mean | 0.2626 | 0.32447 | 0.4069 |
| St.Dev. | 0.1035 | 0.11867 | 0.179 |

Statistical significance of differences was determined by Student's t test (Tables 5 and 6) for paired values, evidencing the existence of significant differences between each mutant and native protein (P=0.0066 for mut-N13 and P=0.0036 for mut-C42).

TABLE 5

Results of Student's "t" test for paired values.

| | mut-N13 | SKC-2 |
|---|---|---|
| Mean | 0.3245 | 0.2626 |
| Variance | 0.0141 | 0.0107 |
| n | 8 | 8 |
| PC | 0.8946 | |
| HMD | 0 | |
| df | 7 | |
| t | 3.295 | |
| P | 0.0066 | |

TABLE 6

Results of Student's "t" test for paired values.

| | mut-C42 | SKC-2 |
|---|---|---|
| Mean | 0.40692 | 0.26262 |
| Variance | 0.03204 | 0.0107 |
| n | 8 | 8 |
| PC | 0.83236 | |
| HMD | 0 | |
| df | 7 | |
| t | 3.73891 | |
| P | 0.0036 | |

Figure 12:
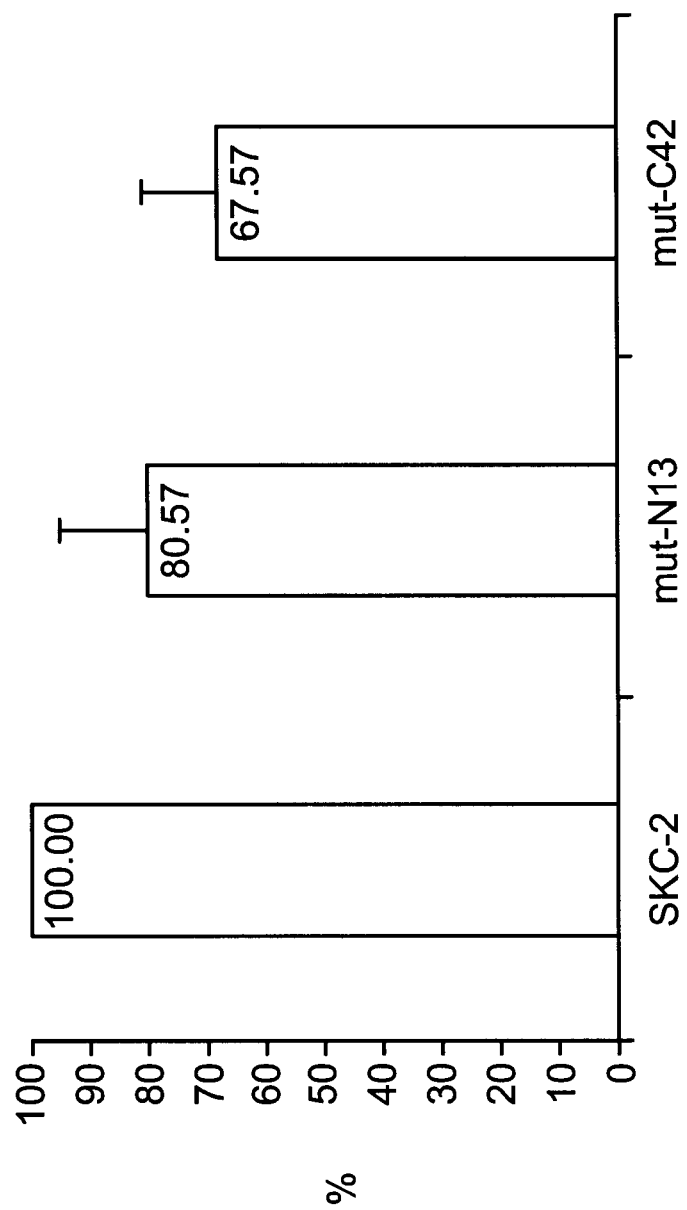

We expressed mut-N13 and mut-C42 ED50 values in terms of percent with respect to SKC-2. Binding of mut-N13 and mut-C42 to human anti-SKC-2 Abs was 80.57% (P=0.0036) and 67.57% (P=0.0001) of reactivity to native SKC-2, respectively (Table 7; FIG. 12).

TABLE 7

$ED_{50}$ values in terms of percent with respect to SKC-2.

| Sera | mut-N13 | mut-C42 |
|---|---|---|
| 6 | 72.633 | 47.131 |
| 7 | 80.173 | 47.55 |
| 12 | 73.194 | 80.972 |
| 14 | 76.267 | 71.455 |
| 17 | 75.763 | 71.104 |
| 28 | 86.243 | 81.37 |
| 32 | 66.294 | 66.188 |
| 42 | 114.01 | 74.76 |
| Mean | 80.572 | 67.566 |
| St. Dev. | 14.702 | 13.469 |
| n | 8 | 8 |

TABLE 7-continued $ED_{50}$ values in terms of percent with respect to SKC-2.

| Sera | mut-N13 | mut-C42 |
|---|---|---|
| t | 3.7377 | 6.8111 |
| P | 0.0036 | 0.0001 | c) Neutralizing Activity Assays Using Sera from Patients Treated with Heberkinase®

Figure 13:
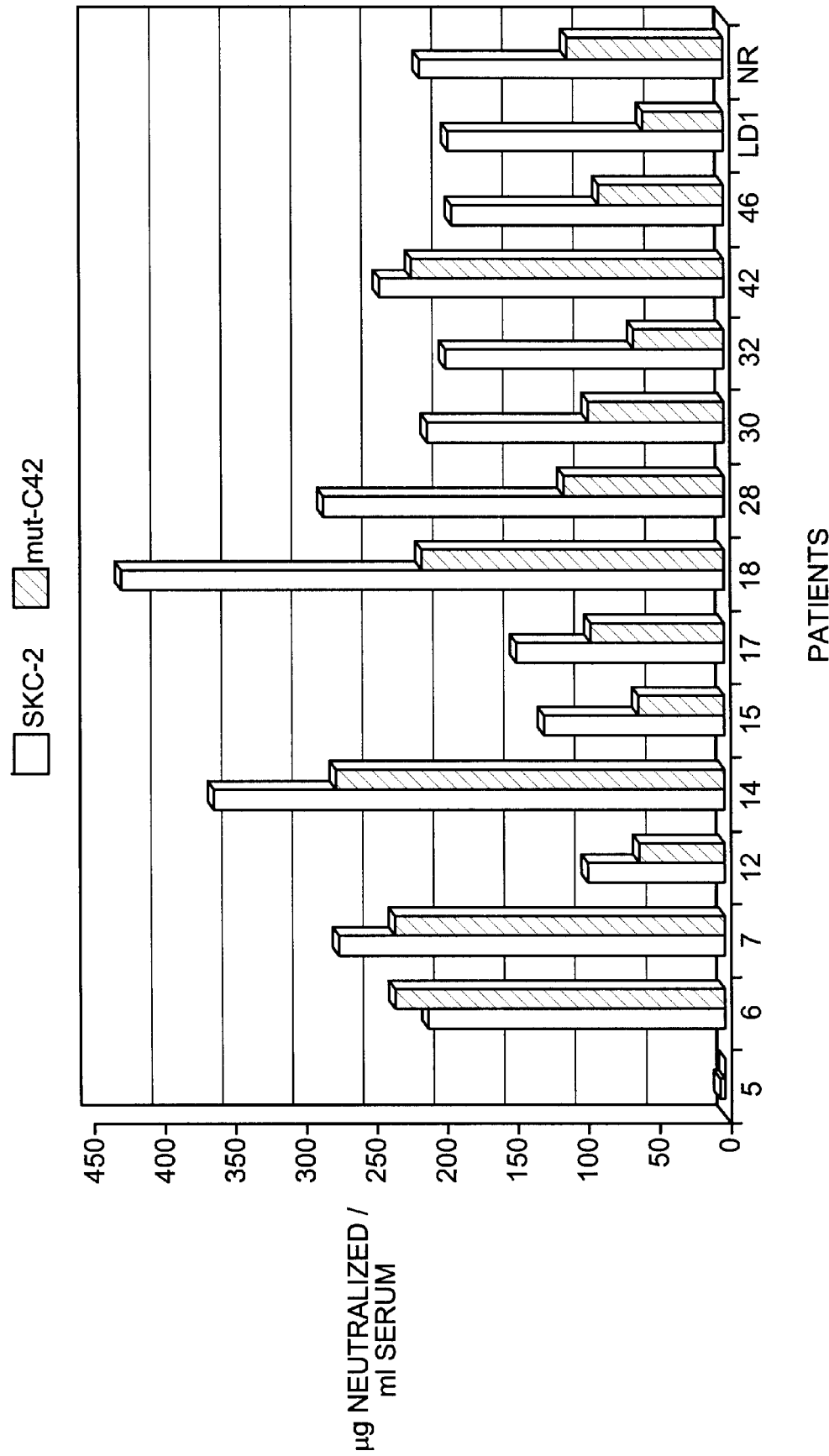

Neutralizing activity titers (NAT) against mut-C42 and native SKC-2 proteins were determined for 15 patients, ten days after Heberkinase® therapy. The chromogenic substrate (S-2251) reaction was performed in polyvinyl plates (Costar, Cambridge, Mass., U.S.A.). Serial dilutions of SKC-2 and mut-C42 (128-2 IU, two-fold dilutions in 20 mM Tris-HCl pH8/0.5M NaCl) were prepared in a volume of 25 μl. Curves were mixed with 25 μl of 1:10 dilutions of each patient serum, and a negative control consisting of a human serum having low anti-SKC-2 Ab titer and preabsorbed with SKC-2. Fifty μl of 25 μg/ml human Plg were added and allowed to mix for 10 min at room temperature. The reaction was developed by addition of 50 μl of chromogenic substrate S-2251 (Chromogenix, Antwerp, Belgium). After incubation for 30 min, the reaction was stopped with 25 μl of 20% acetic acid. Results were measured on a Multiskan system (Titertek, Helsinki, Finland) at 405 nm. The experiment was validated by a standard curve of each protein. All samples were tested by duplicated. The activity required to obtain an absorbance of 0.7 was determined from plots of absorbance versus activity. Neutralizing activity titer (NAT) was determined as the difference between tested serum and negative control values and was expressed as microgrammes of protein neutralized per milliliter of tested serum (FIG. 13). Results were statistically analyzed by the Student's t test for paired values (Table 8).

TABLE 8

Neutralizing Activity Titers (NAT) against SKC-2 and mut-C42 for 15 patients treated with Heberkinase ®.

| Patient | SKC-2 | mut-C42 |
|---|---|---|
| 5 | 2.5928 | 0 |
| 6 | 211.33 | 234.6 |
| 7 | 274.16 | 235.28 |
| 12 | 97.526 | 61.632 |
| 14 | 363.43 | 277.24 |
| 15 | 128.42 | 63.13 |
| 17 | 146.36 | 94.586 |
| 18 | 428.27 | 215.4 |
| 28 | 284.47 | 113.92 |
| 30 | 210.96 | 95.655 |
| 32 | 196.41 | 64.875 |
| 42 | 244.19 | 221.93 |
| 46 | 193.54 | 88.788 |
| LD1 | 196.02 | 59.081 |
| NR | 214 | 110.89 |
| Mean | 212.78 | 129.13 |
| St. Dev. | 103.14 | 84.307 |
| P(test T) | 0.0002 | |

NAT values ranged between 61.63 and 428.27 μg of protein neutralized per ml of tested serum. For most of the individuals mut-C42-NAT decreased with respect to SKC-2-NAT, ranging from 30 to 91% of the native protein value (P=0.0013).

Example 7
Immunological Characterization of mut-C42 Compared to SKC-2. Animals Study Fourteen monkeys (*Cercopithecus aethiops*) of either sex, between two to three years old, weighing 1.8–2.5 kg, were selected for the study. Sera from these monkeys were tested in an anti-SKC-2 ELISA and animals were divided in two groups according to the results:

Group A: eight monkeys without previous anti-SKC-2 Ab titers

Group B: six monkeys with previous anti-SKC-2 Ab titers, probably due to previous contact with streptococcus.

The comparative antigenicity of mutant protein mut-C42 versus native SKC-2 was studied after 850 μg (425 μg/kg of corporal weight) subcutaneous administrations in groups A and B. In each group half of monkeys were treated with mut-C42 and the other half with SKC-2. Humoral response was quantified at week 8 after 4 administrations, for group A; and at week 2 after one administration, for group B. Titration was performed by an anti-SKC-2 ELISA. Polyvinyl plates (Costar, Cambridge, Mass., U.S.A.) were coated with 10 μg/ml SKC-2 in coating buffer (0.1M $Na_2CO_3$, 0.1M $NaHCO_3$, pH 9.6), and incubated overnight at 4° C. Then, plates were washed three times with 0.05% Tween 20 in PBS (PBS-Tween). One hundred μl of serial dilutions (1:2–1:4096, two-fold dilutions in 3% fat-free milk, PBS, 0.05% Tween 20) of each monkey serum were added. After incubation for 1 h at 37° C., plates were incubated with a biotinylated protein A solution at 1:3000 dilution. After incubation for 1 h at 37° C., the binding of monkey Abs to SKC-2 was measured using a horseradish peroxidase-conjugated streptavidin (Sigma) The reaction was developed using 100 μl per well of 1 mg/ml o-phenylenediamine (Sigma), 0.03% $H_2O_2$ in substrate buffer (0.1M citric acid, 0.2M $Na_2HPO_4$, pH 5.0). After 30 min, the reaction was stopped with 50 μl of 4M $H_2SO_4$. Results were measured on a Multiskan system (Titertek, Helsinki, Finland) at 492 nm. The anti-SKC-2 Ab titer was determined as the maximal dilution in which positive signal was obtained. Positive signal was considered when the value was at least two-fold the background.

Anti-SKC-2 Ab titers rose post-treatment, but animals from group B developed titers notably higher than those from group A (Table 9). Ab titers from group A were slightly lower for monkeys treated with mut-C42 compared with those treated with SKC-2. There are two particular monkeys (33 and 85) showing very low Ab titers. Ab titers generated by animals from group B showed no differences between treatments.

TABLE 9

Anti-SKC-2 antibody titers in monkeys treated with SKC-2 or mut-C42

| Treatment | Grup A (week 8) | | Grup B (week 2) | |
|---|---|---|---|---|
| | Animal | Titer | Animal | Titer |
| SKC-2 | 18 | 64 | 3 | 640 |
| | 21 | 50 | 42 | 640 |
| | 73 | 256 | 66 | 240 |
| | 321 | 256 | | |
| | Mean | 156.5 | Mean | 506.66 |
| | St. Dev. | 115.03 | St. Dev. | 230.94 |
| mut-C42 | 6 | 100 | 23 | 640 |
| | 33 | 16 | 26 | 260 |
| | 78 | 256 | 79 | 520 |

TABLE 9-continued

Anti-SKC-2 antibody titers in monkeys treated with SKC-2 or mut-C42

| Treatment | Grup A (week 8) | | Grup B (week 2) | |
|---|---|---|---|---|
| | Animal | Titer | Animal | Titer |
| | 85 | 16 | | |
| | Mean | 97 | Mean | 473.33 |
| | St. Dev. | 113.15 | St. Dev. | 194.25 |

Animal sera were also subjected to a neutralization assay in order to determine their neutralizing activity titer (NAT).

Figure 14:
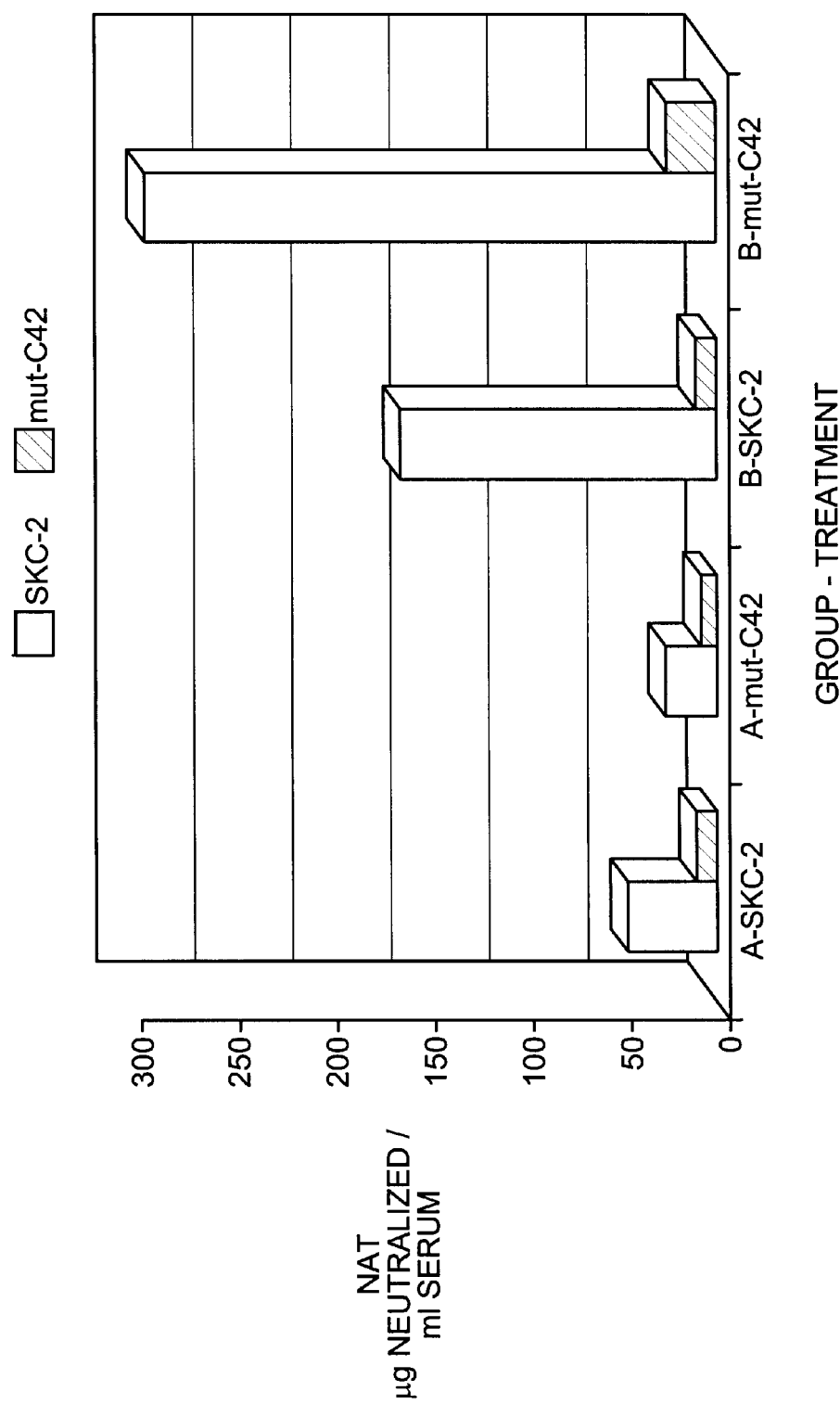

Serial dilutions of SKC-2 and mut-C42 (128-2 IU, two-fold dilutions in 20 mM Tris-HCl pH8/0.5 M NaCl) were prepared in a volume of 25 μl in polyvinyl plates (Costar, Cambridge, Mass., USA). SKC-2 and mut-C42 curves were mixed with 25 μl of each monkey diluted serum and a negative control. For monkeys without previous anti-SKC-2 Ab titer a 1:2 dilution was used, and sera from monkeys with previous anti-SKC-2 Ab titer were diluted 1:5. The negative control was a monkey serum without anti-SKC-2 Ab titer. Fifty μl of 25 μg/ml human pasminogen were added and allowed to mix for 10 min at room temperature. The reaction was developed by addition of 50 μl of chromogenic substrate S-2251 (Chromogenix, Antwerp, Belgium). After incubation for 30 min, the reaction was stopped with 25 μl of 20% acetic acid. Results were measured on a Multiskan system (Titertek, Helsinki, Finland) at 405 nm. The experiment was validated by a standard curve of each protein. All samples were tested by duplicate. The activity required to obtain an absorbance of 0.87 for grup A and 0.37 for grup B, was determined from plots of absorbance versus activity. The neutralizing activity titer (NAT) was determined as the difference between the tested serum and negative control values and was expressed as microgrammes of protein neutralized per milliliter of tested serum (Table 10; FIG. 14).

Abs from most of the monkeys inhibited the formation of SKC-2-Plg and mut-C42-Plg activator complexes in vitro. SKC-2-NAT developed by monkeys from group A were considerably lower than SKC-2 neutralizing capacity exhibited by group B. However, mut-C42-NAT values were similar for both groups.

Monkeys from group A treated with SKC-2 showed NAT values ranging between 35.43 and 54.17 μg (45.3±8.33) of SKC-2 and between 0 and 19.3 μg (9.13±8.47) of mut-C42 moiety neutralized per ml of tested serum. Sera from monkeys treated with mut-C42 elicited NAT values ranging between 6.79 and 44 μg (24.3±20) of SKC-2 and between 0 and 14.12 μg (7.5±8.69) of mut-C42 moiety neutralized per ml of tested serum. Interestingly, animals 33 and 85, showing low anti-SKC-2 Ab titers, exhibited insignificant or none NAT against both proteins.

TABLE 10

Neutralizing Activity Titers (NAT) of monkey sera against SKC-2 and mut-C42 proteins.

| Treatment | | GrupA (week 8) | | | | Grup B (week 2) | | |
|---|---|---|---|---|---|---|---|---|
| | Animal# | SKC-2 | mut-C42 | P | Animal# | SKC-2 | mut-C42 | P |
| SKC-2 | 18 | 35.430 | 12.371 | | 3 | 241.897 | 6.580 | |
| | 21 | 41.806 | 0.000 | | 42 | 89.256 | 0.000 | |
| | 73 | 54.176 | 4.866 | | 66 | 151.102 | 21.708 | |
| | 321 | 49.797 | 19.304 | | | | | |
| | Mean | 45.302 | 9.135 | 0.0042 | Mean | 160.752 | 9.429 | 0.0369 |
| | St. Dev. | 8.339 | 8.477 | | St. Dev. | 76.777 | 11.131 | |
| | 6 | 44.032 | 14.121 | | 23 | 374.112 | 33.905 | |
| mut-C42 | 33 | 6.792 | 0.000 | | 26 | 184.289 | 24.357 | |
| | 78 | 39.084 | 15.881 | | 79 | 313.603 | 15.554 | |
| | 85 | 7.382 | 0.000 | | | | | |
| | Mean | 24.322 | 7.500 | 0.0621 | Mean | 290.668 | 24.605 | 0.0394 |
| | St. Dev. | 20.005 | 8.690 | | St. Dev. | 96.967 | 9.178 | |
| P | | 0.1247 | 0.7967 | | | 0.1467 | 0.1451 | |

Monkeys from group B showed a considerable increase in Ab titers after one administration of the proteins. However, there were no differences in anti-SKC-2 Ab titers between monkeys treated with native and mutant proteins. These animals showed no SKC-2 neutralizing capacity before the treatment. After only one administration of the studied proteins, Abs from most of the monkeys inhibited the formation of SKC-2-Plg and mut-C42-Plg activator complexes in vitro. Monkeys treated with SKC-2 showed NAT values ranging between 89.25 and 241.9 $\mu$g (160.75±76.77) of SKC-2 and between 0 and 21.7 $\mu$g (9.42±11.13) of mut-C42 moiety neutralized per ml of tested serum. Sera from monkeys treated with mut-C42 elicited NAT values ranging between 184.29 and 374.11 $\mu$g (290.67±96.96) of SKC-2 and between 15.55 and 33.9 $\mu$g (24.6±9.17) of mut-C42 moiety neutralized per ml of tested serum.

Statistical analyses supported the following results: (a) mut-C42 was significantly less affected than SKC-2 by neutralizing Abs from monkeys treated with the native protein (P=0.0042 for group A and P=0.0369 for group B), (b) the same result was obtained for group B animals treated with mut-C42 (P=0.0394), (c) in contrast, monkeys from group A receiving mut-C42 treatment showed no significant differences between SKC-2- and mut-C42-neutralizing activities (P=0.0621), and (d) within each group, no statistical significance was obtained from comparison between SKC-2 and mut-C42 treatments.

Statistical significance of the differences for neutralizing activities in monkeys treated with SKC-2 was determined using the Student's t test for paired values, one-tailed distribution. Neutralizing activities of monkeys treated with mut-C42 were analyzed using the Student's t test for paired values, two-tailed distribution. Statistical significance of the differences between SKC-2 and mut-C42 treatments was determined by a Student's t test for two-samples with unequal variances ($P<0.05$).

BRIEF DESCRIPTION OF FIGURES

Streptokinase Mutants

FIG. 1: Schematic representation of the reactivity of patient sera to a spot-synthesized peptide library spanning the whole sequence of SKC-2 protein.

$N_1$: number of patients whose sera reacted with each individual spot.

$N_2$: number of spots recognized by each patient serum.

FIG. 2: Frequency distribution of 1008 samples tested by anti-SKC-2(373–414) Ultra-Micro-ELISA according to their Sample/Positive ratio.

FIG. 3: Plots of Adsorbed/Intact ratio versus Sample/Positive ratio for 140 samples tested in an auxiliary inhibition assay based on previous adsorption with SKC-2 (373–414) peptide.

FIG. 4: Recognition of SKC-2(373–414) peptide by sera from normal donors. Schematic representation of the results.

FIG. 5: Plasmid pEM-1, carrying the sequence of the mutant skc-2-N13 gene under the *E. coli* trytophan promoter, and displaying bacteriophage T4 termination signal at the 3' end of the gene in order to provide higher stability to expression.

FIG. 6: Plasmid pSKH-11, carrying the sequence of the mutant skc-2-N13 gene fused to the coding sequence for Asp-Ile-Val-Asp-Gly-Gly-6xHis tail under the *E. coli* tryptophan promoter, and displaying bacteriophage T4 termination signal at the 3' end of the gene in order to provide higher stability to expression.

FIG. 7: Plasmid pIJ-4, carrying the sequence of the mutant skc-2-C42 under the *E. coli* tryptphan promoter, and displaying bacteriophage T4 termination signal at the 3' end of the gene in order to provide higher stability to expression.

FIG. 8: Plasmid pMC-8, carrying the sequence of the mutant skc-2-C42 gene fused to the coding sequence Asp-Ile-Val-Asp-Gly-Gly-6xHis tail under the *E. coli* tryptophan promoter, and displaying bacteriophage T4 termination signal at the 3' end of the gene in order to provide higher stability to expression.

FIG. 9: mut-N13 and mut-C42 direct binding assay by anti-SKC-2 human antibodies from patients treated with Heberkinase®.

FIG. 10: 50% inhibition (μg/ml) of SKC-2, mut-N13 and mut-C42 for each patient treated with Heberkinase®.

FIG. 11: Mean and standard deviation of values represented in FIG. 10.

FIG. 12: Mean and standard deviation of values represented in FIG. 10 expressed in terms of percent with respect to SKC-2.

FIG. 13: Neutralizing Activity Titer (NAT) against SKC-2 and mut-C42 proteins in patients receiving Heberkinase® therapy.

FIG. 14: Neutralizing Activity Titer (NAT) of monkey sera against SKC-2 and mut-2 proteins.

REFERENCES

Astrup, T. and Mullertz, S. (1952) Arch. Biochem. Biophys 40, 346–351.

Bruserund, O. (1990) APMIS 98, 1077–1084.
Bruserund, O.; Elsayed, S. and Pawelec, G. (1992) Mol. Immunol. 29,1097–1104.
Bruserund, O. L.; Sollid, L. and Foyn-Jorgensen, P. (1986) J. Clin. Lab. Immun. 20, 69–74.
Dagert, M., and Erlich, S. L. (1974) Gene 6: 23–28.
Davies, K. A.; Mathieson, P.; Winearis, C. G.; Rees, A. J.; and Walport, M. J. (1990) Clin.Exp.Immunol.80, 83
Estrada, M. P., Hernández, L., Pérez, A., Rodríguez, P., Serrano, R., Rubiera, R., Pedraza, A.,
Padrón, G., Antuch, W., de la Fuente, J. and Herrera, L. (1992) Biotechnology 10, 1138–1142.
Fiberger, P. (1982) J. Clin. Lab. Invest. 42, Suppl. 162, 49–54.
Frank, R. (1992) Tetrahedron 48, 9217–9212.
Gonzlezgronow, M.; Enghild, J. J.; Pizzo, S. V. (1993) Biochimica rt Biophysica Acta 1180, 283–288
Hanahan, D. (1983) J. Mol. Biol. 166, 557–580.
Maniatis, T.; Frisch, E. F. and Sambrook, J. (1982) Cold Spring Harbor Laboratory, USA.
McGrath, K. G.; Zeffren, B.; Alexander, J.; Kaplan, K. and Patterson, R. (1985) J. Allergy Clin. Immunol. 76, 453
Parhami-Seren, B.; Keel, T. and Reed, G. L. (1996) Hybridoma 15, 169–176
Parhami-Seren, B.; Lynch, M.; White, H. D. and Reed, G. L. (1995) Mol. Immunol. 32, 717–724
Patente europea No. EP 0 489 201 B 1.
U.S. Pat. No. 5,240,845.
Randall, K.; Gelfond, D. H.; Stoffel, S.; Scharf, S.; Higuchi, R.; Horn, G. T.; Mullis, K. B. and Erlich, H. A. (1988) Science 239, 487–491.
Rao, A. K.; Pratt, C.; Berke, A.; Jaffe, A.; Ockene, L.; Schreiber, T. L.; Bell, W. R.; Knaterund, G.; Robertson, T. L. and Terrin, M. L. (1988) J. Am. Coll. Cardiol. 11,1
Reed, G. L.; Kussie, P. and Parhami-Seren, B. (1993) J. Immunol. 150, 4407–4415.
Sanger, F.; Nickler, S. and Coulson, A. K. (1977) Proc. Natl. Acad. Sci. USA 74, 5463–5467.
Schick, L. A. and Castellino, F. J. (1974) Biochem. Biophys. Res. Commun. 57, 47–54
Schweitzer, D. H.; Van der Wall, E. E.; Bosker, H. A.; Scheffer, E. and Macfarlane, J. D. (1991) Cardiology 78, 68.
Sorber, W. A. and Herbst, V. (1988) Cutis 42, 57
Spottl, F. and Kaiser, R. (1974) Thromb. Diath. Haemorrh.32, 608
Tillet, W. S. and Garner, R. L.(1933) J. Exp. Med. 58, 485–502.
Tillet, W. S; Edwards, E. D. and Garner, R. L. (1934) J. Clin. Invest. 13,47–78
Urdahl, K. B.; Mathews, J. D.; Currie, B. (1996) Australian and New Zealand J. Med. 26,49–53
Westtund, L. E. and Anderson, L. O. (1985) Thrombosis Research 37, 213–223.
Youkeles, L. H.; Soliman, M. Y. and Rosenstreich, D. L. (1991) J. Allergy Clin. Immunol. 88, 166–171.

SEQUENCE LISTING

<160> NUMBER OF SEQ ID NOS: 14

<210> SEQ ID NO 1
<211> LENGTH: 401
<212> TYPE: PRT
<213> ORGANISM: Streptococcus equisimilis

<400> SEQUENCE: 1

```
Asn Asn Ser Gln Leu Val Val Ser Val Ala Gly Thr Val Glu Gly Thr
 1               5                  10                  15

Asn Gln Asp Ile Ser Leu Lys Phe Phe Glu Ile Asp Leu Thr Ser Arg
            20                  25                  30

Pro Ala His Gly Gly Lys Thr Glu Gln Gly Leu Ser Pro Lys Ser Lys
        35                  40                  45

Pro Phe Ala Thr Asp Ser Gly Ala Met Pro His Lys Leu Glu Lys Ala
    50                  55                  60

Asp Leu Leu Lys Ala Ile Gln Glu Gln Leu Ile Ala Asn Val His Ser
65                  70                  75                  80

Asn Asp Asp Tyr Phe Glu Val Ile Asp Phe Ala Ser Asp Ala Thr Ile
                85                  90                  95

Thr Asp Arg Asn Gly Lys Val Tyr Phe Ala Asp Lys Asp Gly Ser Val
            100                 105                 110

Thr Leu Pro Thr Gln Pro Val Gln Glu Phe Leu Leu Ser Gly His Val
        115                 120                 125

Arg Val Arg Pro Tyr Lys Glu Lys Pro Ile Gln Asn Gln Ala Lys Ser
    130                 135                 140

Val Asp Val Glu Tyr Thr Val Gln Phe Thr Pro Leu Asn Pro Asp Asp
145                 150                 155                 160
```

-continued

```
Asp Phe Arg Pro Gly Leu Lys Asp Thr Lys Leu Leu Lys Thr Leu Ala
                165                 170                 175

Ile Gly Asp Thr Ile Thr Ser Gln Glu Leu Leu Ala Gln Ala Gln Ser
            180                 185                 190

Ile Leu Asn Lys Thr His Pro Gly Tyr Thr Ile Tyr Glu Arg Asp Ser
        195                 200                 205

Ser Ile Val Thr His Asp Asn Asp Ile Phe Arg Thr Ile Leu Pro Met
    210                 215                 220

Asp Gln Glu Phe Thr Tyr His Val Lys Asn Arg Glu Gln Ala Tyr Glu
225                 230                 235                 240

Ile Asn Lys Lys Ser Gly Leu Asn Glu Glu Ile Asn Asn Thr Asp Leu
                245                 250                 255

Ile Ser Glu Lys Tyr Tyr Val Leu Lys Lys Gly Glu Lys Pro Tyr Asp
            260                 265                 270

Pro Phe Asp Arg Ser His Leu Lys Leu Phe Thr Ile Lys Tyr Val Asp
        275                 280                 285

Val Asn Thr Asn Glu Leu Leu Lys Ser Glu Gln Leu Leu Thr Ala Ser
    290                 295                 300

Glu Arg Asn Leu Asp Phe Arg Asp Leu Tyr Asp Pro Arg Asp Lys Ala
305                 310                 315                 320

Lys Leu Leu Tyr Asn Asn Leu Asp Ala Phe Gly Ile Met Asp Tyr Thr
                325                 330                 335

Leu Thr Gly Lys Val Glu Asp Asn His Asp Thr Asn Arg Ile Ile
            340                 345                 350

Thr Val Tyr Met Gly Lys Arg Pro Glu Gly Glu Asn Ala Ser Tyr His
        355                 360                 365

Leu Ala Tyr Asp Lys Asp Arg Tyr Thr Glu Glu Arg Glu Val Tyr
    370                 375                 380

Ser Tyr Leu Arg Tyr Thr Gly Thr Pro Ile Pro Asp Asn Pro Asn Asp
385                 390                 395                 400

Lys
```

<210> SEQ ID NO 2
<211> LENGTH: 413
<212> TYPE: PRT
<213> ORGANISM: Streptococcus equisimilis

<400> SEQUENCE: 2

```
Asn Asn Ser Gln Leu Val Val Ser Val Ala Gly Thr Val Glu Gly Thr
 1               5                  10                  15

Asn Gln Asp Ile Ser Leu Lys Phe Phe Glu Ile Asp Leu Thr Ser Arg
            20                  25                  30

Pro Ala His Gly Gly Lys Thr Glu Gln Gly Leu Ser Pro Lys Ser Lys
        35                  40                  45

Pro Phe Ala Thr Asp Ser Gly Ala Met Pro His Lys Leu Glu Lys Ala
    50                  55                  60

Asp Leu Leu Lys Ala Ile Gln Glu Gln Leu Ile Ala Asn Val His Ser
65                  70                  75                  80

Asn Asp Asp Tyr Phe Glu Val Ile Asp Phe Ala Ser Asp Ala Thr Ile
                85                  90                  95

Thr Asp Arg Asn Gly Lys Val Tyr Phe Ala Asp Lys Asp Gly Ser Val
            100                 105                 110

Thr Leu Pro Thr Gln Pro Val Gln Glu Phe Leu Leu Ser Gly His Val
        115                 120                 125
```

```
Arg Val Arg Pro Tyr Lys Glu Lys Pro Ile Gln Asn Gln Ala Lys Ser
    130                 135                 140

Val Asp Val Glu Tyr Thr Val Gln Phe Thr Pro Leu Asn Pro Asp Asp
145                 150                 155                 160

Asp Phe Arg Pro Gly Leu Lys Asp Thr Lys Leu Leu Lys Thr Leu Ala
                165                 170                 175

Ile Gly Asp Thr Ile Thr Ser Gln Glu Leu Leu Ala Gln Ala Gln Ser
                180                 185                 190

Ile Leu Asn Lys Thr His Pro Gly Tyr Thr Ile Tyr Glu Arg Asp Ser
            195                 200                 205

Ser Ile Val Thr His Asp Asn Asp Ile Phe Arg Thr Ile Leu Pro Met
    210                 215                 220

Asp Gln Glu Phe Thr Tyr His Val Lys Asn Arg Glu Gln Ala Tyr Glu
225                 230                 235                 240

Ile Asn Lys Lys Ser Gly Leu Asn Glu Glu Ile Asn Asn Thr Asp Leu
                245                 250                 255

Ile Ser Glu Lys Tyr Tyr Val Leu Lys Lys Gly Glu Lys Pro Tyr Asp
                260                 265                 270

Pro Phe Asp Arg Ser His Leu Lys Leu Phe Thr Ile Lys Tyr Val Asp
            275                 280                 285

Val Asn Thr Asn Glu Leu Leu Lys Ser Glu Gln Leu Leu Thr Ala Ser
    290                 295                 300

Glu Arg Asn Leu Asp Phe Arg Asp Leu Tyr Asp Pro Arg Asp Lys Ala
305                 310                 315                 320

Lys Leu Leu Tyr Asn Asn Leu Asp Ala Phe Gly Ile Met Asp Tyr Thr
                325                 330                 335

Leu Thr Gly Lys Val Glu Asp Asn His Asp Asp Thr Asn Arg Ile Ile
                340                 345                 350

Thr Val Tyr Met Gly Lys Arg Pro Glu Gly Glu Asn Ala Ser Tyr His
            355                 360                 365

Leu Ala Tyr Asp Lys Asp Arg Tyr Thr Glu Glu Arg Glu Val Tyr
    370                 375                 380

Ser Tyr Leu Arg Tyr Thr Gly Thr Pro Ile Pro Asp Asn Pro Asn Asp
385                 390                 395                 400

Lys Asp Ile Val Asp Gly Gly His His His His His
                405                 410

<210> SEQ ID NO 3
<211> LENGTH: 372
<212> TYPE: PRT
<213> ORGANISM: Streptococcus equisimilis

<400> SEQUENCE: 3

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
                20                  25                  30

Ile Ser Leu Lys Phe Phe Glu Ile Asp Leu Thr Ser Arg Pro Ala His
            35                  40                  45

Gly Gly Lys Thr Glu Gln Gly Leu Ser Pro Lys Ser Lys Pro Phe Ala
        50                  55                  60

Thr Asp Ser Gly Ala Met Pro His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95
```

```
Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
            115                 120                 125

Thr Gln Pro Val Gln Glu Phe Leu Leu Ser Gly His Val Arg Val Arg
        130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Phe Arg
            165                 170                 175

Pro Gly Leu Lys Asp Thr Lys Leu Leu Lys Thr Leu Ala Ile Gly Asp
            180                 185                 190

Thr Ile Thr Ser Gln Glu Leu Leu Ala Gln Ala Gln Ser Ile Leu Asn
            195                 200                 205

Lys Thr His Pro Gly Tyr Thr Ile Tyr Glu Arg Asp Ser Ser Ile Val
    210                 215                 220

Thr His Asp Asn Asp Ile Phe Arg Thr Ile Leu Pro Met Asp Gln Glu
225                 230                 235                 240

Phe Thr Tyr His Val Lys Asn Arg Glu Gln Ala Tyr Glu Ile Asn Lys
                245                 250                 255

Lys Ser Gly Leu Asn Glu Glu Ile Asn Asn Thr Asp Leu Ile Ser Glu
            260                 265                 270

Lys Tyr Tyr Val Leu Lys Lys Gly Glu Lys Pro Tyr Asp Pro Phe Asp
        275                 280                 285

Arg Ser His Leu Lys Leu Phe Thr Ile Lys Tyr Val Asp Val Asn Thr
    290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335

Tyr Asn Asn Leu Asp Ala Phe Gly Ile Met Asp Tyr Thr Leu Thr Gly
            340                 345                 350

Lys Val Glu Asp Asn His Asp Asp Thr Asn Arg Ile Ile Thr Val Tyr
        355                 360                 365

Met Gly Lys Arg
    370

<210> SEQ ID NO 4
<211> LENGTH: 384
<212> TYPE: PRT
<213> ORGANISM: Streptococcus equisimilis

<400> SEQUENCE: 4

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Pro His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95
```

-continued

```
Tyr Phe Glu Val Ile Asp Phe Ala Ser Asp Ala Thr Ile Thr Asp Arg
            100                 105                 110
Asn Gly Lys Val Tyr Phe Ala Asp Lys Asp Gly Ser Val Thr Leu Pro
        115                 120                 125
Thr Gln Pro Val Gln Glu Phe Leu Leu Ser Gly His Val Arg Val Arg
    130                 135                 140
Pro Tyr Lys Glu Lys Pro Ile Gln Asn Gln Ala Lys Ser Val Asp Val
145                 150                 155                 160
Glu Tyr Thr Val Gln Phe Thr Pro Leu Asn Pro Asp Asp Phe Arg
                165                 170                 175
Pro Gly Leu Lys Asp Thr Lys Leu Leu Lys Thr Leu Ala Ile Gly Asp
                180                 185                 190
Thr Ile Thr Ser Gln Glu Leu Leu Ala Gln Ala Gln Ser Ile Leu Asn
            195                 200                 205
Lys Thr His Pro Gly Tyr Thr Ile Tyr Glu Arg Asp Ser Ser Ile Val
210                 215                 220
Thr His Asp Asn Asp Ile Phe Arg Thr Ile Leu Pro Met Asp Gln Glu
225                 230                 235                 240
Phe Thr Tyr His Val Lys Asn Arg Glu Gln Ala Tyr Glu Ile Asn Lys
                245                 250                 255
Lys Ser Gly Leu Asn Glu Ile Asn Asn Thr Asp Leu Ile Ser Glu
            260                 265                 270
Lys Tyr Tyr Val Leu Lys Lys Gly Glu Lys Pro Tyr Asp Pro Phe Asp
        275                 280                 285
Arg Ser His Leu Lys Leu Phe Thr Ile Lys Tyr Val Asp Val Asn Thr
    290                 295                 300
Asn Glu Leu Leu Lys Ser Glu Gln Leu Leu Thr Ala Ser Glu Arg Asn
305                 310                 315                 320
Leu Asp Phe Arg Asp Leu Tyr Asp Pro Arg Asp Lys Ala Lys Leu Leu
                325                 330                 335
Tyr Asn Asn Leu Asp Ala Phe Gly Ile Met Asp Tyr Thr Leu Thr Gly
                340                 345                 350
Lys Val Glu Asp Asn His Asp Asp Thr Asn Arg Ile Ile Thr Val Tyr
            355                 360                 365
Met Gly Lys Arg Asp Ile Val Asp Gly Gly His His His His His
        370                 375                 380

<210> SEQ ID NO 5
<211> LENGTH: 30
<212> TYPE: DNA
<213> ORGANISM: Streptococcus equisimilis

<400> SEQUENCE: 5
ggaattcatg aacaacagcc aattagttgt                                   30

<210> SEQ ID NO 6
<211> LENGTH: 30
<212> TYPE: DNA
<213> ORGANISM: Streptococcus equisimilis

<400> SEQUENCE: 6
cggatcctta tttgtcgtta gggttatcag                                   30

<210> SEQ ID NO 7
<211> LENGTH: 27
<212> TYPE: DNA
<213> ORGANISM: Streptococcus equisimilis
```

<400> SEQUENCE: 7
cgatatcttt gtcgttaggg ttatcag                                27

<210> SEQ ID NO 8
<211> LENGTH: 29
<212> TYPE: DNA
<213> ORGANISM: Streptococcus equisimilis

<400> SEQUENCE: 8
ggaattcatg attgctggac ctgagtggc                              29

<210> SEQ ID NO 9
<211> LENGTH: 30
<212> TYPE: DNA
<213> ORGANISM: Streptococcus equisimilis

<400> SEQUENCE: 9
cggatcctta tcgcttgccc atataaacgg                             30

<210> SEQ ID NO 10
<211> LENGTH: 27
<212> TYPE: DNA
<213> ORGANISM: Streptococcus equisimilis

<400> SEQUENCE: 10
cgatatctcg cttgcccata taaacgg                                27

<210> SEQ ID NO 11
<211> LENGTH: 1209
<212> TYPE: DNA
<213> ORGANISM: Streptococcus equisimilis

<400> SEQUENCE: 11
atgaacaaca gccaattagt tgttagcgtt gctggtactg ttgagggggac gaatcaagac      60 attagtctta aattttttga aattgaccta acatcacgac ctgctcatgg aggaaagaca     120
gagcaaggct taagtccaaa atcaaaacca tttgctactg atagtggcgc gatgccacat     180
aaacttgaaa aagctgactt actaaaggct attcaagaac aattgatcgc taacgtccac     240
agtaacgacg actactttga ggtcattgat tttgcaagcg atgcaaccat tactgatcga     300
aacggcaagg tctactttgc tgacaaagat ggttcggtaa ccttgccgac ccaacctgtc     360
caagaatttt tgctaagcgg acatgtgcgc gttagaccat ataaagaaaa accaatacaa     420
aatcaagcga atctgttga tgtggaatat actgtacagt ttactcccctt aaaccctgat     480 gacgatttca gaccaggtct caaagatact aagctattga aaacactagc tatcggtgac     540
accatcacat ctcaagaatt actagctcaa gcacaaagca ttttaaacaa acccacccca     600
ggctatacga tttatgaacg tgactcctca atcgtcactc atgacaatga cattttccgt     660
acgattttac caatggatca agagtttact taccatgtca aaaatcggga caagcttat      720 gagatcaata aaaatctgg tctgaatgaa gaaataaaca cactgaccct gatctctgag     780
aaatattacg tccttaaaaa agggaaaag ccgtatgatc cctttgatcg cagtcacttg     840
aaactgttca ccatcaaata cgttgatgtc aacaccaacg aattgctaaa agcgagcag     900 ctcttaacag ctagcgaacg taacttagac ttcagagatt tatacgatcc tcgtgataag     960
gctaaactac tctacaacaa tctcgatgct tttggtatta tggactatac cttaactgga    1020
aaagtagagg ataatcacga tgacaccaac cgtatcataa ccgtttatat gggcaagcga    1080
cccgaaggag agaatgctag ctatcattta gcctatgata aagatcgtta taccgaagaa    1140

-continued

```
gaacgagaag tttacagcta cctgcgttat acagggacac ctatacctga taaccctaac    1200
gacaaataa                                                             1209
```

<210> SEQ ID NO 12
<211> LENGTH: 1245
<212> TYPE: DNA
<213> ORGANISM: Streptococcus equisimilis

<400> SEQUENCE: 12

```
atgaacaaca gccaattagt tgttagcgtt gctggtactg ttgaggggac gaatcaagac      60
attagtctta aatttttga aattgaccta acatcacgac ctgctcatgg aggaaagaca     120
gagcaaggct taagtccaaa atcaaaacca tttgctactg atagtggcgc gatgccacat     180
aaacttgaaa aagctgactt actaaaggct attcaagaac aattgatcgc taacgtccac     240
agtaacgacg actactttga ggtcattgat tttgcaagcg atgcaaccat tactgatcga     300
aacggcaagg tctactttgc tgacaaagat ggttcggtaa ccttgccgac ccaacctgtc     360
caagaatttt tgctaagcgg acatgtgcgc gttagaccat aaagaaaaa accaatacaa     420 aatcaagcga aatctgttga tgtggaatat actgtacagt ttactcccct aaaccctgat     480
gacgatttca gaccaggtct caaagatact aagctattga aaacactagc tatcggtgac     540
accatcacat ctcaagaatt actagctcaa gcacaaagca ttttaaacaa aacccaccca     600
ggctatacga tttatgaacg tgactcctca atcgtcactc atgacaatga cattttccgt     660
acgattttac caatggatca agagtttact taccatgtca aaaatcggga acaagcttat     720
gagatcaata aaaaatctgg tctgaatgaa gaaataaaca cactgacct gatctctgag      780 aaatattacg tccttaaaaa aggggaaaag ccgtatgatc cctttgatcg cagtcacttg     840
aaactgttca ccatcaaata cgttgatgtc aaccaacg aattgctaaa agcgagcag        900 ctcttaacag ctagcgaacg taacttagac ttcagagatt tatacgatcc tcgtgataag     960
gctaaactac tctacaacaa tctcgatgct tttggtatta tggactatac cttaactgga    1020
aaagtagagg ataatcacga tgacaccaac cgtatcataa ccgtttatat gggcaagcga    1080
cccgaaggag agaatgctag ctatcatta gcctatgata aagatcgtta taccgaagaa     1140
gaacgagaag tttacagcta cctgcgttat acagggacac ctatacctga taaccctaac    1200
gacaaagata tcgtcgacgg ggggcaccac caccaccacc actaa                    1245
```

<210> SEQ ID NO 13
<211> LENGTH: 1122
<212> TYPE: DNA
<213> ORGANISM: Streptococcus equisimilis

<400> SEQUENCE: 13

```
atgattgctg gacctgagtg gctgctagac cgtccatctg tcaacaacag ccaattagtt      60
gttagcgttg ctggtactgt tgagggacg aatcaagaca ttagtcttaa attttttgaa     120
attgacctaa catcacgacc tgctcatgga ggaaagacag agcaaggctt aagtccaaaa    180
tcaaaaccat ttgctactga tagtggcgcg atgccacata aacttgaaaa agctgactta    240
ctaaaggcta ttcaagaaca attgatcgct aacgtccaca gtaacgacga ctactttgag    300
gtcattgatt ttgcaagcga tgcaaccatt actgatcgaa acggcaaggt ctactttgct    360
gacaaagatg gttcggtaac cttgccgacc caacctgtcc aagaattttt gctaagcgga    420
catgtgcgcg ttagaccata aagaaaaa ccaatacaaa atcaagcgaa atctgttgat      480
```

-continued

| | |
|---|---|
| gtggaatata ctgtacagtt tactcccttg aaccctgatg acgatttcag accaggtctc | 540 |
| aaagatacta agctattgaa aacactagct atcggtgaca ccatcacatc tcaagaatta | 600 |
| ctagctcaag cacaaagcat tttaaacaaa acccacccag gctatacgat ttatgaacgt | 660 |
| gactcctcaa tcgtcactca tgacaatgac attttccgta cgattttacc aatggatcaa | 720 |
| gagtttactt accatgtcaa aaatcgggaa caagcttatg agatcaataa aaaatctggt | 780 |
| ctgaatgaag aaataaacaa cactgacctg atctctgaga aatattacgt ccttaaaaaa | 840 |
| ggggaaaagc cgtatgatcc ctttgatcgc agtcacttga aactgttcac catcaaatac | 900 |
| gttgatgtca acaccaacga attgctaaaa agcgagcagc tcttaacagc tagcgaacgt | 960 |
| aacttagact tcagagattt atacgatcct cgtgataagg ctaaactact ctacaacaat | 1020 |
| ctcgatgctt ttggtattat ggactatacc ttaactggaa aagtagagga taatcacgat | 1080 |
| gacaccaacc gtatcataac cgtttatatg ggcaagcgat aa | 1122 |

<210> SEQ ID NO 14
<211> LENGTH: 1158
<212> TYPE: DNA
<213> ORGANISM: Streptococcus equisimilis

<400> SEQUENCE: 14

| | |
|---|---|
| atgattgctg gacctgagtg gctgctagac cgtccatctg tcaacaacag ccaattagtt | 60 |
| gttagcgttg ctggtactgt tgaggggacg aatcaagaca ttagtcttaa attttttgaa | 120 |
| attgacctaa catcacgacc tgctcatgga ggaaagacag agcaaggctt aagtccaaaa | 180 |
| tcaaaaccat ttgctactga tagtggcgcg atgccacata acttgaaaaa gctgacttaa | 240 |
| ctaaaggcta ttcaagaaca attgatcgct aacgtccaca gtaacgacga ctactttgag | 300 |
| gtcattgatt ttgcaagcga tgcaaccatt actgatcgaa acggcaaggt ctactttgct | 360 |
| gacaaagatg gttcggtaac cttgccgacc caacctgtcc aagaattttt gctaagcgga | 420 |
| catgtgcgcg ttagaccata taagaaaaaa ccaatacaaa atcaagcgaa atctgttgat | 480 |
| gtggaatata ctgtacagtt tactcccttg aaccctgatg acgatttcag accaggtctc | 540 |
| aaagatacta agctattgaa aacactagct atcggtgaca ccatcacatc tcaagaatta | 600 |
| ctagctcaag cacaaagcat tttaaacaaa acccacccag gctatacgat ttatgaacgt | 660 |
| gactcctcaa tcgtcactca tgacaatgac attttccgta cgattttacc aatggatcaa | 720 |
| gagtttactt accatgtcaa aaatcgggaa caagcttatg agatcaataa aaaatctggt | 780 |
| ctgaatgaag aaataaacaa cactgacctg atctctgaga aatattacgt ccttaaaaaa | 840 |
| ggggaaaagc cgtatgatcc ctttgatcgc agtcacttga aactgttcac catcaaatac | 900 |
| gttgatgtca acaccaacga attgctaaaa agcgagcagc tcttaacagc tagcgaacgt | 960 |
| aacttagact tcagagattt atacgatcct cgtgataagg ctaaactact ctacaacaat | 1020 |
| ctcgatgctt ttggtattat ggactatacc ttaactggaa aagtagagga taatcacgat | 1080 |
| gacaccaacc gtatcataac cgtttatatg ggcaagcgag atatcgtcga cggggggcac | 1140 |
| caccaccacc accactaa | 1158 |

What is claimed is:

1. A method for producing streptokinase mutants by expression of a gene encoding said mutant streptokinase which comprises the steps of transforming a host cell with an expression vector containing a streptokinase gene skc-2 fragment consisting essentially of the nucleotide sequence (Seq. ID. No. 11):

```
ATGAACAACA GCCAATTAGT TGTTAGCGTT GCTGGTACTG        60
TTGAGGGGAC GAATCAAGAC
ATTAGTCTTA AATTTTTGA AATTGACCTA ACATCACGAC        120
CTGCTCATGG AGGAAAGACA
GAGCAAGGCT TAAGTCCAAA ATCAAAACCA TTTGCTACTG        180
ATAGTGGCGC GATGCCACAT
AAACTTGAAA AAGCTGACTT ACTAAAGGCT ATTCAAGAAC        240
AATTGATCGC TAACGTCCAC
AGTAACGACG ACTACTTTGA GGTCATTGAT TTTGCAAGCG        300
ATGCAACCAT TACTGATCGA
AACGGCAAGG TCTACTTTGC TGACAAAGAT GGTTCGGTAA        360
CCTTGCCGAC CCAACCTGTC
CAAGAATTTT TGCTAAGCGG ACATGTGCGC GTTAGACCAT        420
ATAAAGAAAA ACCAATACAA
AATCAAGCGA AATCTGTTGA TGTGGAATAT ACTGTACAGT        480
TTACTCCCTT AAACCCTGAT
GACGATTTCA GACCAGGTCT CAAAGATACT AAGCTATTGA        540
AAACACTAGC TATCGGTGAC
ACCATCACAT CTCAAGAATT ACTAGCTCAA GCACAAAGCA        600
TTTTAAACAA AACCCACCCA
GGCTATACGA TTTATGAACG TGACTCCTCA ATCGTCACTC        660
ATGACAATGA CATTTTCCGT
ACGATTTTAC CAATGGATCA AGAGTTTACT TACCATGTCA        720
AAAATCGGGA ACAAGCTTAT
GAGATCAATA AAAAATCTGG TCTGAATGAA GAAATAAACA        780
ACACTGACCT GATCTCTGAG
AAATATTACG TCCTTAAAAA AGGGGAAAAG CCGTATGATC        840
CCTTTGATCG CAGTCACTTG
AAACTGTTCA CCATCAAATA CGTTGATGTC AACACCAACG        900
AATTGCTAAA AAGCGAGCAG
CTCTTAACAG CTAGCGAACG TAACTTAGAC TTCAGAGATT        960
TATACGATCC TCGTGATAAG
GCTAAACTAC TCTACAACAA TCTCGATGCT TTTGGTATTA       1020
TGGACTATAC CTTAACTGGA
AAAGTAGAGG ATAATCACGA TGACACCAAC CGTATCATAA       1080
CCGTTTATAT GGGCAAGCGA
CCCGAAGGAG AGAATGCTAG CTATCATTTA GCCTATGATA       1140
AAGATCGTTA TACCGAAGAA
GAACGAGAAG TTTACAGCTA CCTGCGTTAT ACAGGGACAC       1200
CTATACCTGA TAACCCTAAC
GACAAATAA                                         1209
``` wherein said streptokinase mutants have reduced antigenicity compared to a full length SKC-2 streptokinase.

2. A method for producing streptokinase mutants by expression of a gene encoding said mutant streptokinase which comprises the steps of transforming a host cell with an expression vector containing a streptokinase gene skc-2 fragment fused to the sequence tail Asp-Ile-Val-Asp-Gly-Gly-6xHis consisting essentially of the nucleotide sequence (Seq. ID. No. 12):

```
AACAACAGCC AATTAGTTGT TAGCGTTGCT GGTACTGTTG AGGGGACGAA TCAAGACATT         60
AGTCTTAAAT TTTTTGAAAT TGACCTAACA TCACGACCTG CTCATGGAGG AAAGACAGAG        120
CAAGGCTTAA GTCCAAAATC AAAACCATTT GCTACTGATA GTGGCGCGAT GCCACATAAA        180
CTTGAAAAAG ACGACTTACT AAAGGCTATT CAAGAACAAT TGATCGCTAA CGTCCACAGT        240
AACGACGACT CATTTGAGGT CATTGATTTT GCAAGCGATC GAACCATTAC TGATCGAAAC        300
GGCAAGGTCT ACTTTGCTGA CAAAGATGGT TCGGTAACCT TGCCGACCCA ACCTGTCCAA        360
GAATTTTTGC TAAGCGGACA TGTGCGCGTT AGACCATATA AGAAAAACC AATACAAAAT        420
CAAGCGAAAT CTGTTGATGT GGAATATACT GTACAGTTTA CTCCCTTAAA CCCTGATGAC        480
GATTTCAGAC CAGGTCTCAA AGATACTAAG CTATTGAAAA CACTAGCTAT CGGTGACACC        540
ATCACATCTC AAGAATTACT AGCTCAAGCA CAAAGCATTT TAAACAAAAC CCACCCAGGC        600
```

```
                              -continued
TATACGATTT ATGAACGTGA CTCCTCAATC GTCACTCATG ACAATGACAT TTTCCGTACG    660

ATTTTACCAA TGGATCAAGA GTTTACTTAC CATGTCAAAA ATCGGGAACA AGCTTATGAG    720

ATCAATAAAA AATCTGGTCT GAATGAAGAA ATAAACAACA CTGACCTGAT CTCTGAGAAA    780

TATTACGTCC TAAAAAAAGG GGAAAAGCCC TATGATCCCT TTGATCGCAG TCACTTGAAA    840

CTGTTCACCA TCAAATACGT TGATGTCAAC ACCAACGAAT TGCTAAAAAG CGAGCAGCTC    900

TTAACAGCTA GCGAACGTAA CTTAGACTTC AGAGATTTAT ACGATCCTCG TGATAAGGCT    960

AAACTACTCT ACAACAATCT CGATGCTTTT GGTATTATGG ACTATACCTT AACTGGAAAA   1020

GTAGAGGATA ATCACGATGA CACCAACCGT ATCATAACCG TTTATATGGG CAAGCGAGCC   1080

GAAGGAGAGA ATGCTAGCTA TCATTTAGCC TATGATAAAG ATGCTTATAC CGAAGAAGAA   1140

CGAGAAGTTT ACAGCTACCT GCGTTATACA GGGACACCTA TACCTGATAA CCCTAACGAC   1200

AAATAAGATA TCGTCGACGG GGGGCACCAC CACCACCACC ACTAA                   1245
```

3. A method for producing streptokinase mutants by expression of a gene encoding said mutant streptokinase which comprises the steps of transforming a host cell with an expression vector containing a streptokinase gene skc-2 fragment consisting essentially of the nucleotide sequence (Seq. ID. No. 13):

```
ATGATTGCTG GACCTGAGTG GCTGCTAGAC CGTCCATCTG TCAACAACAG CCAATTAGTT     60

GTTAGCGTTG CTGGTACTGT TGAGGGACG AATCAAGACA TTAGTCTTAA ATTTTTTGAA     120

ATTGACCTAA CATCACGACC TGCTCATGGA GGAAAGACAG AGCAAGGCTT AAGTCCAAAA    180

TCAAAACCAT TTGCTACTGA TAGTGGCGCG ATGCCACATA AACTTGAAAA AGCTGACTTA    240

CTAAAGGCTA TTCAAGAACA ATTGATCGCT AACGTCCACA GTAACGACGA CTACTTTGAG    300

GTCATTGATT TTGCAAGCGA TGCAACCATT ACTGATCGAA ACGGCAAGGT CTACTTTGCT    360

GACAAAGATG GTTCGGTAAC CTTGCCGACG CAACCTGTCC AAGAATTTTT GCTAAGCGGA    420

CATGTGCGCG TTAGACCATA TAAAGAAAAA CCAATACAAA ATCAAGCGAA ATCTGTTGAT    480

GTGGAATATA CTGTACAGTT TACTCCCTTA AACCCTGATG ACGATTTCAG ACCAGGTCTC    540

AAAGATACTA AGCTATTGAA AACACTAGCT ATCGGTGACA CCATCACATC TCAAGAATTA    600

CTAGCTCAAG CACAAAGCAT TTTAAACAAA ACCCACCCAG GCTATACGAT TTATGAACGT    660

GACTCCTCAA TCGTCACTCA TGACAATGAC ATTTTCCGTA CGATTTTACC AATGGATCAA    720

GAGTTTACTT ACCATGTCAA AAATCGGGAA CAAGCTTATG AGATCAATAA AAAATCTGGT    780

CTGAATGAAG AAATAAACAA CACTGACCTG ATCTCTGAGA AATATTACGT CCTTAAAAAA    840

GGGGAAAAGC CGTATGATCC CTTTGATCGC AGTCACTTGA AACTGTTCAC CATCAAATAC    900

GTTGATGTCA ACACCAACGA ATTGCTAAAA AGCGAGCAGC TCTTAACAGC TAGCGAACGT    960

AACTTAGACT TCAGAGATTT ATACGATCCT CGTGATAAGG CTAAACTACT CTACAACAAT   1020

CTCGATGCTT TTGGTATTAT GGACTATACC TTAACTGGAA AAGTAGAGGA TAATCACGAT   1080

GACACCAACC GTATCATAAC CGTTTATATG GGCAAGCGAT AA                       1122
``` wherein said streptokinase mutants have reduced antigenicity compared to a full length SKC-2 streptokinase.

4. A method for producing streptokinase mutants by expression of a gene encoding said mutant streptokinase which comprises the steps of transforming a host cell with an expression vector containing a streptokinase gene skc-2 fragment fused to the sequence tail Asp-Ile-Val-Asp-Gly-Gly-6xHis consisting essentially of the nucleotide sequence (Seq. ID. No. 14):

```
ATGATTGCTG GACCTGAGTG GCTGCTAGAC CGTCCATCTG TCAACAACAG CCAATTAGTT      60

GTTAGCGTTG CTGGTACTGT TGAGGGGACG AATCAAGACA TTAGTCTTAA ATTTTTTGAA     120

ATTGACCTAA CATCACGACC TGCTCATGGA GGAAAGACAG AGCAAGGCTT AAGTCCAAAA     180

TCAAAACCAT TTGCTACTGA TAGTGGCGCG ATGCCACATA AACTTGAAAA AGCTGACTTA     240

CTAAAGGCTA TTCAAGAACA ATTGATCGCT AACGTCCACA GTAACGACGA CTACTTTGAG     300

GTCATTGATT TTGCAAGCGA TGCAACCATT ACTGATCGAA ACGGCAAGGT CTACTTTGCT     360

GACAAAGATG GTTCGGTAAC CTTGCCGACC CAACCTGTCC AAGAATTTTT GCTAAGCGGA     420

CATGTGCGCG TTAGACCATA TAAAGAAAAA CCAATACAAA ATCAAGCGAA ATCTGTTGAT     480

GTGGAATATA CTGTACAGTT TACTCCCTTA AACCCTGATG ACGATTTCAG ACCAGGTCTC     540

AAAGATACTA AGCTATTGAA AACACTAGCT ATCGGTGACA CCATCACATC TCAAGAATTA     600

CTAGCTCAAG CACAAAGCAT TTTAAACAAA ACCCACCCAG GCTATACGAT TTATGAACGT     660

GACTCCTCAA TCGTCACTCA TGACAATGAC ATTTTCCGTA CGATTTTACC AATGGATCAA     720

GAGTTTACTT ACCATGTCAA AAATCGGGAA CAAGCTTATG AGATCAATAA AAAATCTGGT     780

CTGAATGAAG AAATAAACAA CACTGACCTG ATCTCTGAGA AATATTACGT CCTTAAAAAA     840

GGGGAAAAGC CGTATGATCC CTTTGATCGC AGTCACTTGA AACTGTTCAC CATCAAATAC     900

GTTGATGTCA ACACCAACGA ATTGCTAAAA AGCGAGCAGC TCTTAACAGC TAGCGAACGT     960

AACTTAGACT TCAGAGATTT ATACGATCCT CGTGATAAGG CTAAACTACT CTACAACAAT    1020

CTCGATGCTT TTGGTATTAT GGACTATACC TTAACTGGAA AAGTAGAGGA TAATCACGAT    1080

GACACCAACC GTATCATAAC CGTTTATATG GGCAAGCGAG ATATCGTCGA CGGGGGGCAC    1140

CACCACCACC ACCACTAA                                                  1158
```

5. The method of claims 1 or 3 wherein said skc-2 gene fragments are isolated from plasmid pEKG-3.

6. The method of claims 1 or 2 or 3 or 4 wherein said host cell is a bacterium.

7. The method of claim 6 wherein said bacterium is *E. coli*.

8. The method of claim 6 wherein said bacterium is *Escherichia coli* strain W3110.

9. The method of claim 1 wherein said expression vector is a plasmid containing the skc-2 gene fragment operably linked to the *E. coli* tryptophan promoter and the T4 transcription terminator.

10. The method of claim 2 wherein said expression vector is a plasmid containing the skc-2 gene fragment fused to the sequence tail Asp-Ile-Val-Asp-Gly-Gly-6xHis operably linked to the *E. coli* tryptophan promoter and the T4 transcription terminator.

11. The method of claim 3 wherein said expression vector is a plasmid containing the skc-2 gene fragment operably linked to the *E. coli* tryptophan promoter and the T4 transcription terminator.

12. The method of claim 4 wherein said expression vector is a plasmid containing the skc-2 gene fragment fused the sequence tail Asp-Ile-Val-Asp-Gly-Gly-6xHis operably linked to the *E. coli* tryptophan promoter and the T4 transcription terminator.

13. The method of claim 9 wherein said expression vector is the plasmid pEMI-1.

14. The method of claim 10 wherein said expression vector is the plasmid pSKH-11.

15. The method of claim 11 wherein said expression vector is the plasmid pIJ-4.

16. The method of claim 12 wherein said expression vector is the plasmid pMC-8.

17. An isolated and purified nucleic acid consisting essentially of the nucleotide sequence shown in claim 1 wherein said streptokinase mutants have reduced antigenicity compared to a full length SKC-2 streptokinase.

18. An isolated and purified nucleic acid consisting essentially of the nucleotide sequence shown in claim 2.

19. An isolated and purified nucleic acid consisting essentially of the nucleotide sequence shown in claim 3 wherein said streptokinase mutants have reduced antigenicity compared to a full length SKC-2 streptokinase.

20. An isolated and purified nucleic acid consisting essentially of the nucleotide sequence shown in claim 4.

21. An expression vector for the expression of streptokinase mutant SKC-2-N13 in a host cell, said vector containing a streptokinase gene skc-2 fragment consisting essentially of the nucleotide sequence shown in claim 1 operably linked to an effective promoter and transcription terminator wherein said streptokinase mutants have reduced antigenicity compared to a full length SKC-2 streptokinase.

22. An expression vector for the expression of streptokinase mutant SKC-2-N13 in a host cell, said vector containing a streptokinase gene skc-2 fragment fused to the sequence tail Asp-Ile-Val-Asp-Gly-Gly-6xHis consisting essentially of the nucleotide sequence shown in claim 2 operably linked to an effective promoter and transcription terminator.

23. An expression vector for the expression of streptokinase mutant SKC-2-C42 in a host cell, said vector containing a streptokinase gene skc-2 fragment consisting essentially of the nucleotide sequence shown in claim 3 operably linked to an effective promoter and transcription terminator wherein said streptokinase mutants have reduced antigenicity compared to a full length SKC-2 streptokinase.

24. An expression vector for the expression of streptokinase mutant SKC-2-C42 in a host cell, said vector containing a streptokinase gene skc-2 fragment fused to the sequence tail Asp-Ile-Val-Asp-Gly-Gly-6xHis consisting essentially of the nucleotide sequence shown in claim 4 operably linked to an effective promoter and transcription terminator.

25. The expression vector of claim 21 containing the skc-2 gene fragment operably linked to the *E. coli* tryptophan promoter and the T4 transcription terminator for expression of said skc-2 gene fragment in bacteria.

26. The expression vector of claim 22 containing the skc-2 gene fragment fused to the sequence tail Asp-Ile-Val-Asp-Gly-Gly-6xHis operably linked to the *E. coli* tryptophan promoter and the T4 transcription terminator for expression of said skc-2 gene fragment in bacteria.

27. The expression vector of claim 23 containing the skc-2 gene fragment operably linked to the *E. coli* tryptophan promoter and the T4 transcription terminator for expression of said skc-2 gene fragment in bacteria.

28. The expression vector of claim 24 containing the skc-2 gene fragment fused to the sequence tail Asp-Ile-Val-Asp-Gly-Gly-6xHis operably linked to the *E. coli* tryptophan promoter and the T4 transcription terminator for expression of said skc-2 gene fragment in bacteria.

29. The expression vector of claim 25, which is the plasmid pEMI-1, contained in *E. coli*.

30. The expression vector of claim 26, which is the plasmid pSKH-11, contained in *E. coli*.

31. The expression vector of claim 27, which is the plasmid pIJ-4, contained in *E. coli*.

32. The expression vector of claim 28, which is the plasmid pMC-8, contained in *E. coli*.

33. A host cell for producing streptokinase mutant by expression of a gene encoding said streptokinase mutant, said host cell being transformed with an expression vector containing a streptokinase gene skc-2 fragment consisting essentially of the nucleotide sequence shown in claim 1 operably linked to an effective promoter and transcription terminator wherein said streptokinase mutants have reduced antigenicity compared to a full length SKC-2 streptokinase.

34. A host cell for producing streptokinase mutant by expression of a gene encoding said streptokinase mutant, said host cell being transformed with an expression vector containing a streptokinase gene skc-2 fragment fused to the sequence tail Asp-Ile-Val-Asp-Gly-Gly-6xHis consisting essentially of the nucleotide sequence shown in claim 2 operably linked to an effective promoter and transcription terminator.

35. A host cell for producing streptokinase mutant by expression of a gene encoding said streptokinase mutant, said host cell being transformed with an expression vector containing a streptokinase gene skc-2 fragment consisting essentially of the nucleotide sequence shown in claim 3 operably linked to an effective promoter and transcription terminator wherein said streptokinase mutants have reduced antigenicity compared to a full length SKC-2 streptokinase.

36. A host cell for producing streptokinase mutant by expression of a gene encoding said streptokinase mutant, said host cell being transformed with an expression vector containing a streptokinase gene skc-2 fragment fused to the sequence tail Asp-Ile-Val-Asp-Gly-Gly-6xHis consisting essentially of the nucleotide sequence shown in claim 4 operably linked to an effective promoter and transcription terminator.

37. The host cell of claim 33 which is a bacterium.

38. The host cell of claim 34 which is a bacterium.

39. The host cell of claim 35 which is a bacterium.

40. The host cell of claim 36 which is a bacterium.

41. The host cell of claim 37 which is *E. coli*.

42. The host cell of claim 38 which is *E. coli*.

43. The host cell of claim 39 which is *E. coli*.

44. The host cell of claim 40 which is *E. coli*.

45. The host cell of claim 41, which is *E. coli*, strain W3110.

46. The host cell of claim 42, which is *E. coli*, strain W3110.

47. The host cell of claim 43, which is *E. coli*, strain W3110.

48. The host cell of claim 44, which is *E. coli*, strain W3110.

49. The transformed host cell of claim 45, which is transformed clone WSK-N13.

50. The transformed host cell of claim 46, which is transformed clone WSK-N13-H.

51. The transformed host cell of claim 47, which is transformed clone WSK-C42.

52. The transformed host cell of claim 48, which is transformed clone WSK-C42-H.

* * * * *